(12) United States Patent
Annest

(10) Patent No.: US 9,622,864 B2
(45) Date of Patent: *Apr. 18, 2017

(54) IMPLANTABLE SCAFFOLDING CONTAINING AN ORIFICE FOR USE WITH A PROSTHETIC OR BIO-PROSTHETIC VALVE

(71) Applicant: Lon Sutherland Annest, New York, NY (US)

(72) Inventor: Lon Sutherland Annest, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/624,053

(22) Filed: Feb. 17, 2015

(65) Prior Publication Data

US 2015/0164641 A1 Jun. 18, 2015

Related U.S. Application Data

(62) Division of application No. 12/798,629, filed on Apr. 8, 2010, now Pat. No. 8,986,370.

(60) Provisional application No. 61/168,279, filed on Apr. 10, 2009.

(51) Int. Cl.
*A61F 2/24* (2006.01)
*A61B 17/04* (2006.01)
*A61B 17/00* (2006.01)

(52) U.S. Cl.
CPC ........ *A61F 2/2466* (2013.01); *A61B 17/0469* (2013.01); *A61F 2/2409* (2013.01); *A61F 2/2427* (2013.01); *A61F 2/2445* (2013.01); *A61B 2017/003* (2013.01); *A61B 2017/00349* (2013.01); *A61F 2/246* (2013.01); *A61F 2/2412* (2013.01); *A61F 2/2457* (2013.01); *A61F 2250/0003* (2013.01); *A61F 2250/0006* (2013.01)

(58) Field of Classification Search
CPC .... A61F 2/2466; A61F 2/2409; A61F 2/2418; A61F 2/2427; A61F 2/2445; A61F 2/246
See application file for complete search history.

(56) References Cited

U.S. PATENT DOCUMENTS

| 6,419,696 B1 | 7/2002 | Ortiz et al. |
| 6,569,196 B1 * | 5/2003 | Vesely .................. A61F 2/2409 623/1.24 |
| 8,986,370 B2 | 3/2015 | Annest |
| 9,011,522 B2 | 4/2015 | Annest |
| 2006/0074484 A1 | 4/2006 | Huber |

FOREIGN PATENT DOCUMENTS

| EP | 2416739 | 2/2012 |
| WO | WO2010/117471 | 10/2010 |

\* cited by examiner

*Primary Examiner* — Thomas McEvoy
(74) *Attorney, Agent, or Firm* — R. Neil Sudol; Henry D. Coleman

(57) ABSTRACT

In a surgical method for improving cardiac function, an implantable scaffold or valve support device is inserted inside a patient's heart and attached to the heart in a region about a natural mitral valve. The scaffold or valve support device defines an orifice and, after the attaching of the scaffold or valve support device to the heart, a prosthetic or bio-prosthetic valve is seated in the orifice. The scaffold or valve support device is at least indirectly secured to cordae tendenae of the heart.

10 Claims, 19 Drawing Sheets

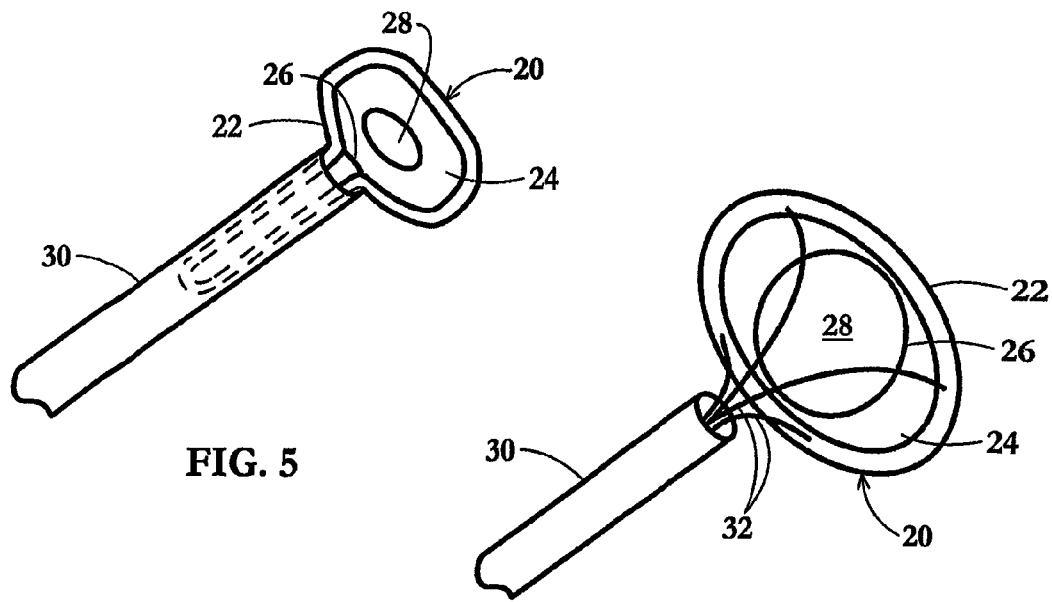
FIG. 5
FIG. 6
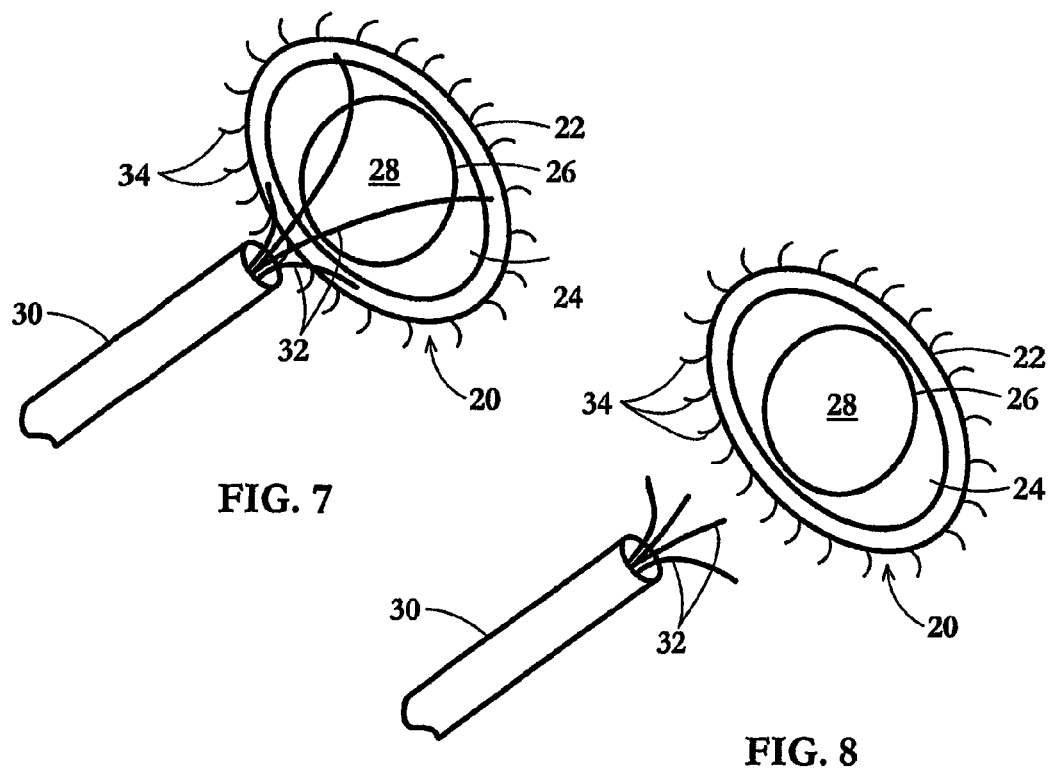
FIG. 7
FIG. 8

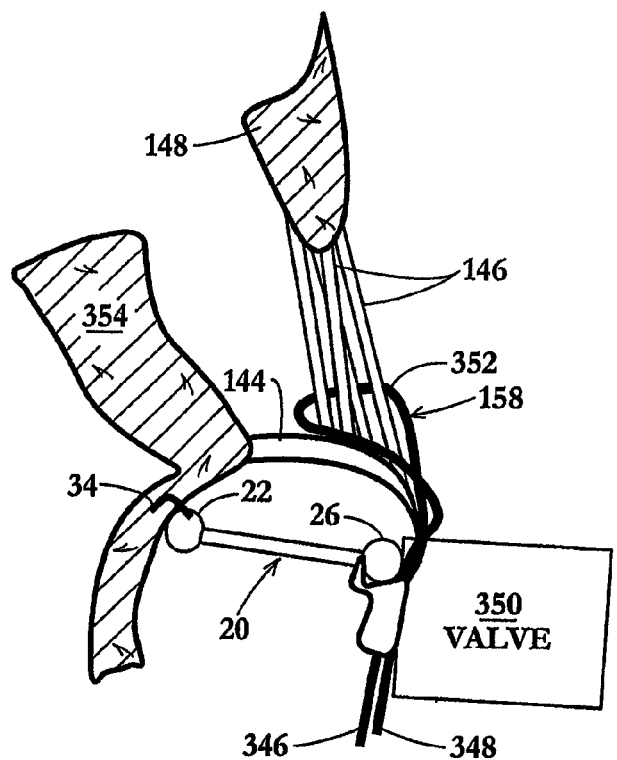
FIG. 38
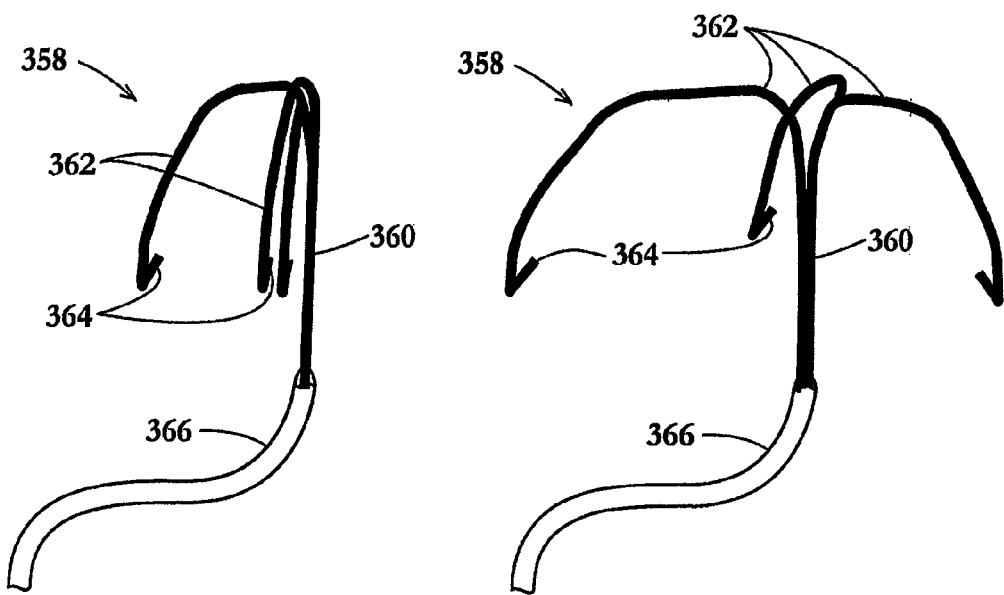
FIG. 39
FIG. 40

IMPLANTABLE SCAFFOLDING CONTAINING AN ORIFICE FOR USE WITH A PROSTHETIC OR BIO-PROSTHETIC VALVE

CROSS-REFERENCE TO RELATED APPLICATION

This application is a division of application Ser. No. 12/798,629 filed Apr. 8, 2010, now U.S. Pat. No. 8,986,370. This application also claims the benefit of U.S. Provisional Patent Application No. 61/168,279 filed Apr. 10, 2009.

FIELD OF THE INVENTION

The present invention relates to medical devices and procedures, in particular related to the replacement of a heart valve, and more particularly, to a novel device for use in a novel procedure for performing a catheter-based heart valve replacement.

BACKGROUND OF THE INVENTION

The four valves of the human heart consist of either two or three pliable leaflets attached circumferentially to a fibrous skeletal annulus. Normally, they function to open in one portion of the cardiac cycle, either systole or diastole, (depending on the valve), causing minimal resistance to forward blood flow, but close by hinging from the annulus during the other part of the cardiac cycle, with the leaflets (either two or three) coming into central contact with each other, such that retrograde flow is inhibited.

Heart valve regurgitation, or leakage occurs when the leaflets of the valve fail to come fully into contact. This can be congenital, or the result of a disease process. Regardless of the cause, the leakage interferes with heart function, since it allows the unintended flow of blood back through the valve. Depending on the degree of leakage, the backward flow can become a self-destructive influence on not only function, but also cardiac geometry. Alternatively, abnormal cardiac geometry can cause the leakage, and the two processes are "cooperative" in causing acceleration of abnormal cardiac function.

The result of a valve having significant regurgitation is that a pathological state develops in which blood may be simultaneously pumped both forward through the out flow valve of a chamber and backward through the inflow valve, decreasing forward cardiac output. Depending on the severity of the leakage, this efficiency of the heart to pump adequate blood flow can be compromised. The process can be caused by myocardial infarction damaging papillary muscles located in the left ventricle, torn or abnormally elongated chordae tendineae, damaged valve structures by infection, degenerative processes, or stretching of the annulus such that leaflets no longer come into contact by virtue of the increased cross-sectional area. Stretching of the ventricle and increased distance between the papillary muscles can also cause leakage of the atrio-ventricular (A/V) valves.

At present, regurgitant valves can be either surgically repaired or replaced, both currently requiring open-heart surgery, use of cardio-pulmonary bypass and stoppage of the heart. Because of the magnitude of the procedure, risk of death, stroke, and bleeding, respiratory, renal, and other complications is significant enough that many patients are not candidates for treatment. The heart or aorta must be cut open, and even when performed by very experienced surgeons, repairs can fail early, or, if initially successful, are not always durable over time.

In the case of the mitral valve, replacement is associated with a higher operative mortality than repair, but does not result in recurrent regurgitation experienced after a repair. The higher mortality is thought to be the result of loss of the function of the papillary muscles of the left ventricle, which are attached to the mitral valve leaflets by cords known as chordae tendineae, which contribute to tethering of the leaflets and systolic shortening of the left ventricle. However, with preservation of these sub-valvular structures, the outcomes equalize, or may be better in severe cases with replacement and sub-valvular structure preservation. (See *Ann Thorac Surg* 2 81: 1153-61.)

Even though the prognosis of surgically untreated mitral regurgitation is poor, (see *N Engl J Med* 2 352:875-83), only 33% of patients with significant regurgitation are referred, due to age, co-morbidities, or physician preference (see *European Journal of Cardio-thoracic Surgery* 34 (2) 935-936).

In the face of a severe, life threatening pathological process with no treatment offered to a majority of patients due to the magnitude of the risks of currently available therapy, a simpler, less invasive approach to treatment, such as a percutaneous device that can effectively eliminate regurgitation, yet preserve annulo-ventricular in atrio-ventricular connectivity, and function is severely needed.

For this reason, there is widespread development currently underway for placement of valves into the aortic (see *Circulation* Dec 2002 p. 3006-3008), and Pulmonary, (see *J. Am. Coll. Card.*, vol. 39, May 15, 2002, p. 1664-1669), positions. There are currently a variety of technologies for aortic replacement, but all generally have an expandable support structure for attached pliable leaflets, delivered either through the apex of the ventricle or retrograde through the aorta from the femoral artery (*The Journal of Thoracic and Cardiovascular Surgery*, October 2008, p 817-819).

Because of the asymmetry of the annuli, as well as the lack of rigidity, the same principals cannot be applied to the mitral and tricuspid valves. In the mitral position, several approaches have been pursued. Additionally, in the case of the mitral valve, radial expansion of a prosthetic replacement could impinge on the aortic valve, with which it shares a portion of its annulus along the anterior leaflet.

Primarily, remodeling of the mitral annulus by various means has been a focus of intense interest. The most advanced are those that rely on the perceived anatomic proximity between the posterior annulus and the coronary sinus (see Webb, et al). Although promising, the coronary sinus has been shown to in all cases to course on the atrial side of the mitral annular plane, and averages 7 to 11 mm from the annulus, and the distances are variable. Moreover, the distances increase in subjects with mitral regurgitation. (See Choure, et al, *J Am. Coll. Card.*; Vol. 48, No. 10, 2.)

Another approach is the central apposition of the anterior and posterior leaflets at the midpoint, mimicking the so-called "Alfieri stitch". The benefit comes from creation of central coaptation.

In general, current heart valve replacement procedures generally require invasive surgery. This of course is a long, difficult and complex process and requires that the patient endure significant, invasive surgery. While various alternatives have been proposed to minimize this trauma, there is still a need in the art to further reduce such potential injury.

The present invention seeks to provide an apparatus and device, which could avoid such traumatic surgery and instead provide for a more limited intrusion by utilizing a catheter to deliver and assemble the heart valve components in-situ.

SUMMARY OF THE INVENTION

The present invention contemplates a device attached to the inside of the heart or a blood vessel, which serves as a scaffold or support for mounting a modular or staple prosthetic valve element to a patient or subject. The scaffold or support device comprises a generally rounded or somewhat oval body member, symmetric or asymmetric in two dimensions, but generally flat in the third dimension, though all components of the scaffold can move independently in or out of the plane. The device is bordered by a pliable, conforming margin, which is generally continuous around the perimeter of the device and is able to take on a variety of shapes such that it can conform to the topography of a heart wall to which the device is being attached. The device can be permanently fixed to the tissue.

Within the plane of the margin, and circumferentially attached to it, is a pliant membrane, such that the margin attached to the heart tissue and the membrane inside the margin together create a barrier. The barrier would be obstructive to blood flow, were it not for the placement of an orifice in roughly the center of the membrane, which is generally round and flexible but generally inelastic. The orifice provides a neo-annulus into which a prosthetic or other valve can be inserted and attached to the scaffold or support device. The device of the present invention provides a means of placing a valve into a site adjacent to a native valve annulus through a means unencumbered by the limitations of the native valve annulus.

With certain valves in the heart, (specifically the atrio-ventricular valves), the sub-valvular structures are important for chamber function. It has been recommended, therefore, when replacement is performed rather than repair, that these structures be incorporated into the annulus of the new valve. (See M. A. Borger, et al *Ann Thoracic Surg* 2 81:1153-1161.) The current invention includes a device and method for incorporation of these structures into the scaffolding, thereby preserving ventriculo-annular contribution to systolic function.

The invention also provides a delivery system and a means by which the margin of the device can be fixed to the tissue of a heart or vessel wall, in one embodiment generally over or behind a heart valve. The orifice within the membranous part of this device then serves as a round neo-annulus into which a valve can be placed.

Recently there has been prolific development and testing of expandable heart valves, which can be inserted by way of a catheter passed either through the vessels and into the heart, or directly across the apex of the left ventricle. The designs vary but generally involve radial expansion of a crimped valve into the desired location by an inflatable balloon, two inflatable gaskets at the inflow and outflow ends, or self-expanding outer ring housing the valve, and others. Such devices are, however, reliably placed only into a nearly circular annulus, ideally with the presence of calcification for rigidity, as in the aortic position, or where the annulus is round with significant length for placement, as in the pulmonary position. The atrio-ventricular (A/V) valves, such as the mitral and tricuspid, are large, irregularly shaped, usually not calcified, and are connected to a sub-valvular apparatus which may contribute to ventricular function. The mitral valve and tricuspid valves are not amenable to current expandable valve designs, and there is great need to treat A/V valve disease not available even with emerging technologies. The mitral valve and tricuspid valves are not amenable to current expandable valve designs, and there is great need to treat A/V valve disease not available even with emerging technologies. The current invention provides a round, fixed annulus attached to atrial or vessel tissue adjacent to the valve, creating a means of deploying expandable valves into the atrio-ventricular position. The invention also provides for a means of incorporating the sub-valvular structures. It includes an implantable scaffold providing a round annulus, a fixation mechanism, a delivery system for remote placement, and a system for incorporation of the sub-valvular apparatus into the neo-annulus. A method for placement is provided.

Accordingly, the present invention comprises an implantable component, including a fixation system, and a delivery system that places the implantable into the heart.

The system may utilize a catheter to enable heart valve placement in a subject by creating a neo-annulus into which a prosthetic valve may subsequently be placed. The system comprises an implantable scaffolding consisting in large part of an outer conformable margin which can be shaped in-situ to match the contours of the surface where the valve will be located, a membranous portion within the margin, and within the membranous portion, an orifice, the orifice creating the neo-annulus which will be used to support placement of a prosthetic or bio-prosthetic valve. A catheter is preferably be used to deliver, position and shape the scaffold to conform to the shape of the desired chamber of the heart, for example, using multiple guide wires attached to various portions of the outer margin, or other appropriate means. These may be used as manipulators to adjust the shape and position of the scaffold, and to hold it in position while the outer margin is fixed to the adjacent tissue surface. The outer margin could be pre-assembled with fixation elements, which are engaged after the scaffold is in position. In any case, the outer margin is fixed circumferentially to the tissue, to create a continuous or near continuous contact between the tissue and the scaffold.

In some embodiments and applications, there is a separate, third component, which provides a means of tethering the sub-valvular apparatus into an orifice of the implantable element in order to take advantage of any potential contribution of the sub-valvular apparatus to cardiac function.

The implantable scaffold or valve-support device can be housed inside a catheter-based delivery system, so that it can be steered through the vascular system. Alternatively, the implantable valve scaffold could be placed in the desired location under a direct, open surgical approach, for example, if surgery were required to address other issues. The implantable component is collapsible for delivery, and self-expandable or manually expanded so that it can enlarge substantially once released from the catheter lumen. Using image guidance, the implantable component is released from the catheter lumen into the appropriate position in the heart chamber or vessel, where the scaffolding device is expanded from a collapsed insertion configuration to an opened use configuration, molded or deformed to conform to the geometry of the cardiac or vascular walls at the implantation site, and permanently attached to the tissue around which valve placement is desired.

The implantable portion then forms a permanent platform into which a valve can be inserted, either acutely, or at some remote time. In most cases, the placement is located adjacent to a native valve, though in one embodiment, the implantable scaffold is attached directly to the leaflets. (In this latter embodiment and others, the membrane portion of the scaffold may be omitted.) The implantable component is, in general, a flexible, generally round but variably shaped membrane which is fixed at its outer margins to the walls of a heart chamber so that it becomes continuous with those walls, allowing forward flow of blood from the chamber to proceed only through an orifice in the membrane surface to allow for placement of a valve, which in the principal embodiment, is a separate structure.

The orifice designed for placement of the valve may have fixation elements incorporated into the margin to facilitate valve adherence. The margin of the orifice may be either flexible or inflexible with respect to its circumference, will generally be inelastic to facilitate expansion of a valve, and may be rounded or irregularly shaped and asymmetric, as appropriate to the valve morphology. In general, the combination of the implantable component and the subsequently placed valve will create complete separation between the chamber of fixation proximal and distal to the membrane margins, except for flow through the valve.

For purposes of facilitating a surface substantial enough to allow fixation of a valve, the orifice acting as the neo-annulus may have a cylindrical configuration, creating a surface rather than a rim, or a so-called "landing zone". The cylindrical surface of the annulus extends perpendicularly to the plane of the membrane portion of the scaffold device and the plane of the native mitral annulus and in alignment with or parallel to the blood flow. The cylinder may be composed of metal mesh, inelastic cloth, material elastic in only one plane (the plane of the blood-flow), a coil, or other appropriate material.

The cylindrical surface may be an integral part of the implanted scaffold, or may be attached by a separate step at some time-point after the scaffold has been deployed. Fixation to the orifice may be by compression, hooks, barb, adhesives, or other appropriate means.

An important feature of the present invention is that the membrane, and indeed the entire valve scaffold, is collapsible, allowing it to be inserted through a catheter. Since the outer margin must conform to a potentially irregular heart wall while the inner rim will be essentially round, the membrane may have a folded, redundant configuration asymmetrically surrounding the neo-annulus portion. Another is that the outer margin or rim is flexible, though not necessarily elastic, allowing for septation of the host chamber by the membrane, even if the chamber is irregular. Also, the membranous element, extending from the margin to the neo-annulus, should be made of a fabric-like material, such as collagen-impregnated polyester, that is hemostatic, flexible, and promotes cellular in-growth and endothelial coverage.

Yet another feature of the present invention is that the valve scaffold can be entirely suture-less, held in place in contact with the heart tissue by an intrinsic fixation system, including, but not limited to, and expandable stent-like framework, an inflatable ring-component, (as like an inner tube) springs, tissue adhesive, magnets, penetrating hooks, barbs, or other appropriate mechanisms.

In some iterations, the mechanism for fixation of a valve scaffold in accordance with the invention may not be incorporated into the implantable component itself, but be delivered subsequent to positioning of the margin, as with a stapler device or other means of attaching devices to tissue. In other iterations part of the fixation components are incorporated into the margin, while corresponding parts are delivered separately, as with a magnetic strip in the coronary sinus with a magnetic counterpart in the margin of the implantable scaffold.

Fixation of a valve scaffold in accordance with the invention may be further enhanced by placing a device through the right atrium and/or coronary sinus (or even the aorta) in the case of the mitral valve, or the left atrium in the case of the tricuspid valve, the device to provide additional support to margin fixation. In this embodiment, hooks, barbs, magnets, or other fixation mechanisms could be passed from either the coronary sinus and/or right atrium and/or aorta (in the case of the mitral valve) to the implantable portion of the device, or vice versa, such that a tethering component penetrates the wall of the structures, holding the margin of the implantable valve scaffold in place. In some embodiments, a similar extra-cardiac support mechanism may be used.

In another embodiment, there will be two or more positioning tethers. These elements will be attached to the implantable component in such a way as to allow the implantable portion to be manipulated into the desired position. The positioning tethers in this embodiment can be advanced such that a portion of the tether or a separate extension thereon, will advance through the margin when deployed, such that a barbed extension on the tether penetrates into the surrounding tissue creating fixation. In another version, a cork-screw-like element is advanced into the heart wall by twisting the positioning tether as the margin is held in place. In still another, the margin is stapled to the heart wall. In any of these instances, once fixation is achieved, the remainder of the tether is detached and removed. The penetrating, fixation element may be a part of the tether, which is then severed, or may be a separate piece, which is merely manipulated into the tissue, by the tether. The tether may go directly into the margin of the implantable device, or enter at a site more centrally, toward or at the neo-annulus.

In still another embodiment, fixation devices may be advanced over some or all of the positioning tethers, such that when any portion of the margin is in the desired location to the tissue, it can be there affixed.

One iteration has hooks or barbs affixed to the marginal component of the implantable valve scaffold, which when rotated, perforate into surrounding tissue, creating fixation.

A major advantage of the present invention is that it can support placement of a roundish valve into a space where the native valve annulus is not nearly round, as is the case for atrio-ventricular valves. A second major advantage of this invention is that by placing the "neo-annulus" separately from the valve, it will allow delivery through a smaller caliber catheter than would be required if the valve itself had an attached annulus-fixation design.

Additionally, since the orifice is by necessity as large or larger than the valve to be placed subsequently, there can be no obstruction or need to add further support for cardiac function in the interval between placement of a valve scaffold per the present invention and valve placement.

Moreover, since a valve scaffold in accordance with the invention can be placed adjacent to a native, non-stenotic valve, it may not necessary to remove the native valve. The invention is particularly beneficial in insufficient atrio-ventricular valves.

In a principal embodiment, the delivery system includes a catheter with one or more lumens which can be inserted under appropriate image guidance and which delivers the implantable valve scaffold, as well as a mechanism for (1) manipulating the valve scaffold into position, and (2) initiating fixation of the valve scaffold to the tissue. The steering/locking components may be initially attached to the valve scaffold, primarily to the margins at one or more sites, but will be detachable once position is achieved and fixation established.

In the case of atrio-ventricular valves, it may be desirable to incorporate elements for tethering the sub-valvular apparatus, consisting of cordae-tendinea and/or the papillary muscles, to the neo-annulus. This feature of the invention contemplates a method and device for circling either some or all cords and/or a portion or all of the papillary muscles with a tether-like component, such that the force normally exerted by these structures during the cardiac cycle can be transmitted to the newly placed valve.

The sub-valvular tethering pursuant to the invention is generally, but not necessarily, employed at the time of valve implantation, and includes an element that surrounds or otherwise is fastened to one or more of the sub-valvular structures and passes a tether with two or more ends, or otherwise fixes a tension member to the structures. A second end of the tension member of tether is passed through the neo-orifice, the membranous portion, or the margin of the implantable component and fixed thereto. In one iteration, the device itself becomes the component that fixes the sub-valvular apparatus to the implantable valve scaffold; in another, it is a tool, which passes, or otherwise places the fixation component.

This element may also have the function of controlling displacement of a native valve leaflet into an undesirable position, by drawing it toward the newly placed valve.

In an alternative embodiment, the device could be delivered through a ventriculotomy, as in the apex of a ventricular chamber, or other direct entrance through a wall of the heart. As such, delivery and fixation mechanisms are configured to facilitate the approach.

A novel approach for an automated, potentially catheter-based mitral replacement system has been developed, and consists of a collapsible frame into which three pericardial leaflets become housed. The device then forms a rigid annulus for attachment of the leaflets and frame, which when expanded into the native valve, results in a tri-leaflet prosthetic inside the native valve. It attaches to the cusps of the native valve and fuses to them for permanent fixation (see Herrman, et al.).

The current invention differs from existing approaches because the current invention either does not rely on native annular or leaflet structures for placement or support, or, in the embodiment where fixation to the leaflets is sought, the device provides only the neo-annulus and not the valve itself. Additionally, in one embodiment, where fixation is achieved through the coronary sinus, the placement of the implantable valve scaffold takes advantage of, rather than suffers from, the fact that the plane of the sinus regularly resides on the atrial side of the annular plane.

Another differentiator of the current invention is the fact that the contemplated prosthetic valve system is modular. A scaffolding delivered separately from the valve, and therefore using a smaller delivery system then one in which the valve is delivered provides fixation and supplies a neo-annulus, which can support a round, prosthetic valve delivered subsequently. The modular approach allows for a smaller delivery system, since annulus and leaflets are delivered separately.

Still another advantage of the current invention is the inclusion of a device and method for incorporation of the sub-valvular apparatus into the neo-annulus or scaffolding system. This preserves ventriculo-annular function, stabilizes the neo-annulus, and therefore, the implanted valve, and limits the likelihood of systolic anterior motion of the anterior leaflet of the native mitral valve (which is a risk associated with placement of a prosthesis valve inside the native valve).

The device that incorporates the sub-valvular apparatus, in the case of the mitral valve, may be a pre-curved, hollow catheter. When advanced through the delivery system, this component can encircle the papillary muscle or cords. A second, pre-formed component, consisting also of a hollow catheter, then advances in conjunction with the first to align with the open tip of the initial component, such that the tips align, such that a continuous cord, wire, tether, or other appropriate element could be advanced through the first component and retrieved through the second (or vice versa), and a continuous loop of the element can be brought through the neo-annulus or other part of the implantable device in order to recruit the cord contribution to cardiac function into the neo-annulus/scaffold if so desired. Tension applied to the looping component can be adjusted before subsequent fixation to the implantable component or valve.

The mechanism for alignment of the two tips of the components for encircling the sub-valvular apparatus may be through pre-formed geometry of the elements, or by a retrieval system, such as magnets or other means of directing them into contact.

In another embodiment of the invention, the component (s) for encircling the sub-valvular apparatus may be a steerable catheter, which can be directed around the desired structures and an appropriate looping component advanced and retrieved. In an alternative embodiment, the encircling components may include a steerable catheter and a non-steerable catheter, or two or more steerable catheters.

In the principal embodiment of the device, the mechanism for capture of the sub-valvular apparatus includes a pre formed or steerable catheter, passed along the same insertion route as the scaffold implantation catheter or a separate access path. The sub-valvular capture catheter is maneuvered around some or all heads of the papillary muscle, or around some or all of the chordae tendineae attached thereto. The catheter allows passage of a tension member around these structures, which can then be retrieved, creating a continuous loop around the intended structures.

The tension element looping around the sub-valvular structures may be exchanged for a second such member with greater surface area.

In another embodiment, the mechanism for capture of the sub-valvular apparatus includes a hooked or barbed element passed through the valve orifice or directly through the leaflets, attaching to the undersurface of the leaflet near or at the margin, such that it engages the leaflet and/or the cords. Such element may be single or multiple, acting as a single hook or as a multiple-tined rake.

In this embodiment, the element will have one or more extensions that can be incorporated into the scaffolding. This element may be deployed with the implantable valve scaffold, or at a separate time through the same or another catheter.

The major embodiments of the element which captures the sub-valvular apparatus comprise generally one or more tension members from each native valve leaflet. In the case of the mitral valve, one or more tension members are deployed that transmit systolic forces from the posterior leaflet/papillary and one or more are inserted that transmit anterior leaflet/papillary forces. These tension members can each incorporate one or more adjustable hooks or barbs, such that attachment to the neo-annulus can be achieved but subsequently manipulated to an appropriate tension, and by attachment to the neo-annulus itself, systolic papillary function will be transmitted to the replacement valve itself. In the iteration where the neo-annulus is attached directly to the leaflets, the subvalvular apparatus will be captured by the (remaining) chordal attachments to the leaflets, and a separate mechanism will be unnecessary.

The hook, barb, or other mechanism for attaching the scaffold to the sub-valvular apparatus, for the purpose of transmitting ventricular systolic forces to the neo-annulus, may be applied to one or more native valve leaflets, in one or multiple sites, delivered together or in sequence, such that the desired distribution of such forces may be appropriately created. A separate fastener may be advanced over the tension member of the element that captures the sub-valvular apparatus, and may then transmit the forces to the neo-annulus with additional fixation than simply the radial compression from the valve insertion.

BRIEF DESCRIPTION OF THE DRAWINGS

FIG. 5 is a view of a collapsed implantable scaffold in accordance with the present invention emerging from the tip of the delivery system.

FIG. 6 is a view of a completely extruded implantable scaffold in accordance with the present invention, having guide wires that are used to manipulate the scaffold for placing it in position.

FIG. 7 is a view of an implantable scaffold component showing one embodiment for fixing the outer margin to the adjacent tissue walls.

FIG. 8 is a view of the implantable scaffold component of FIG. 7 after fixation, and after release from the catheter delivery system, so that the neo-annulus is now capable of receiving a circular valve prosthesis through the same or another delivery system, though the valve prosthesis could also be surgically implanted.

FIG. 38 is a diagram similar to FIG. 37, showing a fastener or locking element crimped to the two strands of the tether.

FIG. 39 is a side view of a grappling hook for capturing the sub-valvular apparatus in a method in accordance with the present invention.

FIG. 40 is a front view of the grappling hook of FIG. 39.

DETAILED DESCRIPTION

The Summary and Brief Description of the Drawings above are incorporated and reiterated herein.

Figure 1:
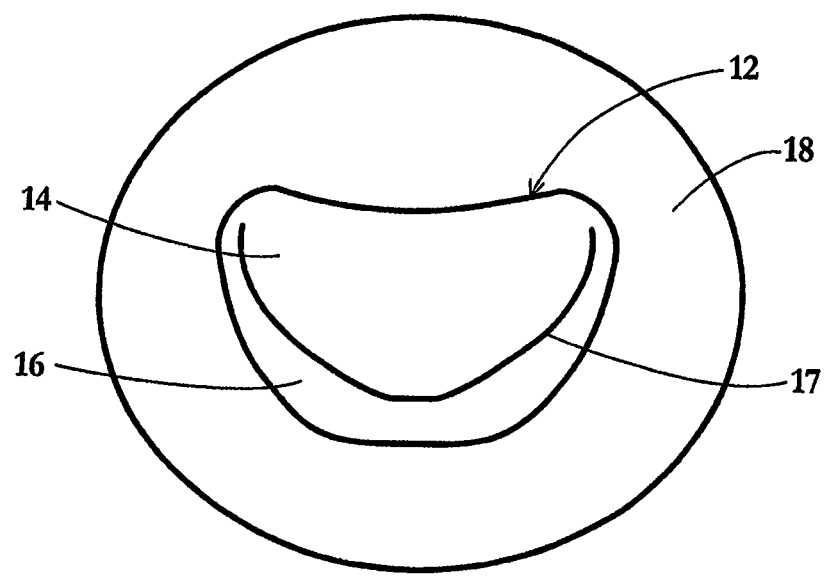
FIG. 1 is a view of the mitral valve from the left atrium.

As depicted in FIG. 1, a mitral valve 12 includes a pair of leaflets or valve flaps 14 and 16 that contact one another along a generally D-shaped set of points 17 in a closed state of the valve. On the atrial side of the valve 12, leaflets are continuous with an internal wall 18 of the atrium.

Figure 2:
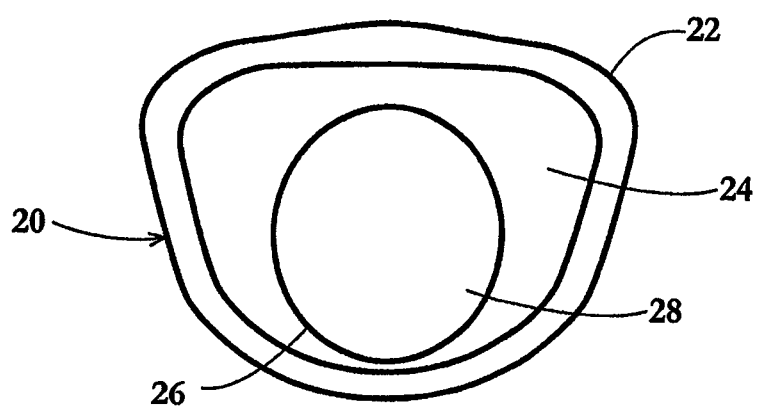
FIG. 2 is a view of a deployed implantable scaffold component in accordance with the present invention, showing an outer margin, a membranous portion, an orifice for valve placement, and a neo-annulus.
Figure 9:
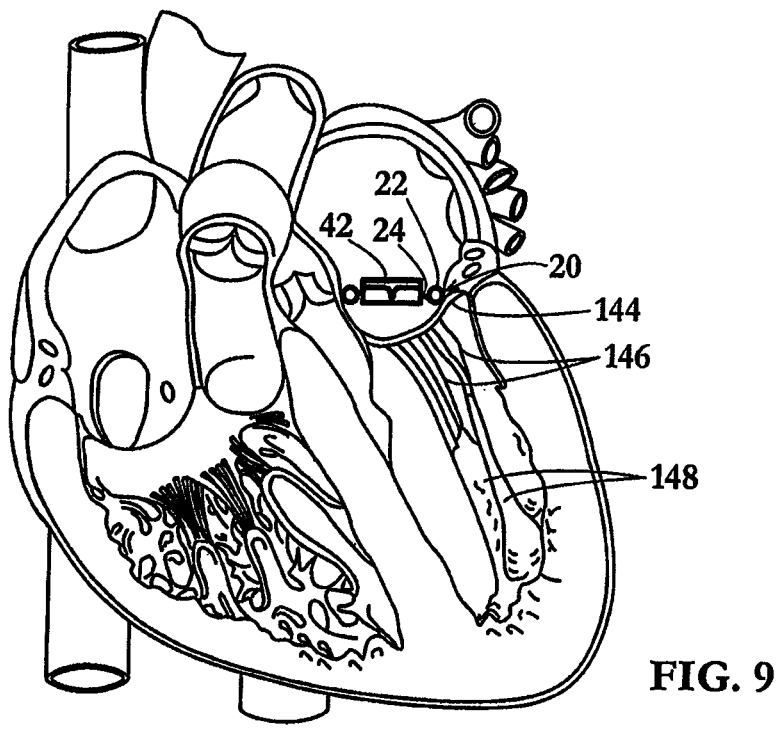
FIG. 9 is a photograph that includes a diagram of an implantable scaffold in accordance with the present invention showing diagrammatically how the implantable margin is fixed at the mitral annulus, an abbreviated membranous portion separating the spaces, and a cylindrical implanted valve with apposed leaflets in profile resides within the neo-annulus.

As depicted in FIG. 2, an implantable valve scaffold or mounting component 20 includes an outer margin or rim element 22, a membranous portion 24, and a generally annular inner margin or rim element 26 defining an orifice 28. Orifice 28 serves as a neo-annulus for receiving or seating a prosthetic or bio-prosthetic valve 42 (FIG. 9). It is contemplated that the valve is a modular or staple article. However, the valve may be custom designed.

It is to be understood that the inner margin or rim element 26 generally has a circular or cylindrical shape, so as to enable the seating of commercially available prosthetic or bio-prosthetic valves, which are circular or cylindrical. The term "annular member" is used herein to denote a continuous or endless configuration that defines an opening, orifice, or aperture. While the opening, orifice, or aperture is typically round or circular, the shape is not necessarily such. An "annular member" as that term is used herein particularly with reference to the element that defines the valve-receiving orifice or neo-annulus, may be oval or even polygonal.

Figure 3:
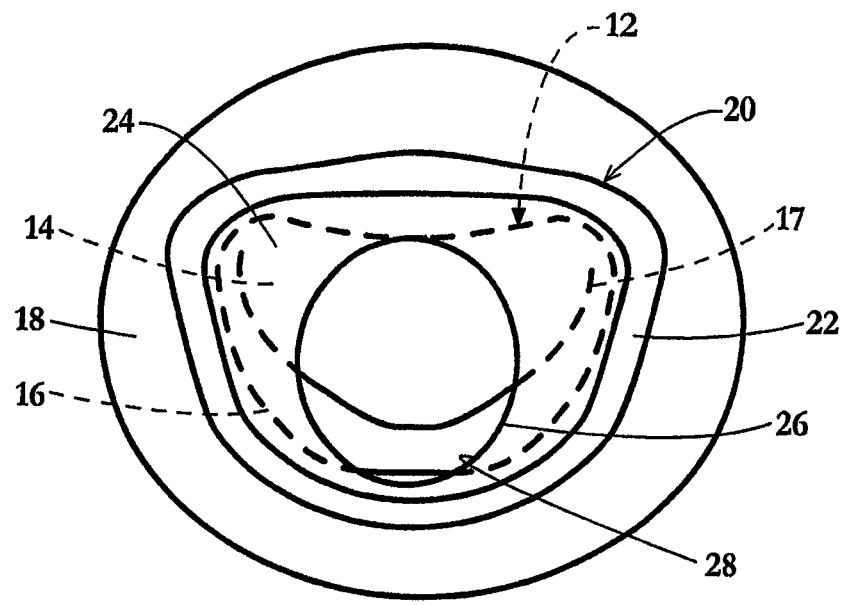
FIG. 3 is a view from the left atrium of the implantable scaffold fixed in position adjacent to a mitral valve.

Scaffold or mounting component 20 is implantable, for example, into the left atrium of a patient's heart, during a procedure to rectify and improve improper valve functioning. FIG. 3 shows scaffold 20 fixed in position over mitral valve 12.

Scaffold or support device 20 is comprises a generally rounded or somewhat oval body member (not separately designated), shown in FIGS. 2 and 3, which symmetric or asymmetric in two dimensions, but generally flat in the third dimension. Outer margin or rim element 22 is a pliable, conforming margin, which is generally continuous around the perimeter of the scaffold 20 and is able to take on a variety of shapes so that it can conform to the topography of the heart wall to which it is being attached. The scaffold device can be permanently fixed to the tissue.

Outer margin or rim element 22 is disposed generally in a plane and circumferentially surrounds pliant membrane 24, such that the margin is attached to the heart tissue and together with the membrane creates a barrier to blood flow. The barrier would be obstructive, were it not for orifice 28 in roughly the center of membrane 24, which is generally round and flexible but generally inelastic. Orifice 28 provides a neo-annulus into which a prosthetic or other valve can be inserted and attached to the scaffold or support device 20. Scaffold 20 provides a means of placing a valve into a site adjacent to a native valve annulus, in a way unencumbered by the limitations of the native valve annulus.

Figure 4:
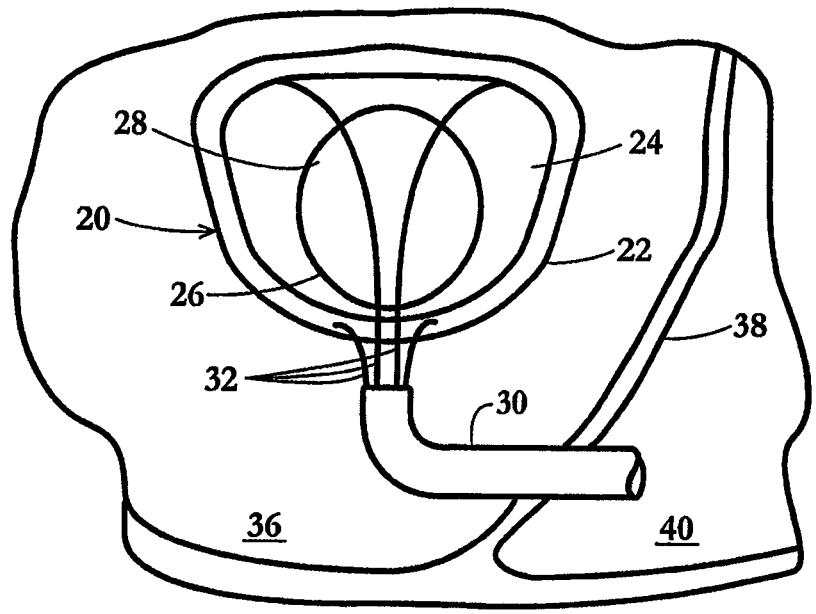
FIG. 4 is a view of a delivery system crossing the inter-atrial septum from the right atrium to deploy the device over the mitral valve.

FIG. 4 illustrates a delivery system and a means by which the outer margin or rim element 22 of scaffold or support device 20 can be fixed to the tissue of a heart or vessel wall, generally over or behind a heart valve such as mitral valve 12 of FIGS. 1 and 2. The delivery system includes a delivery catheter 30 and a plurality of guide wires, filaments, or cords 32 that are removably connected at their distal ends to outer margin or rim element 22. Guide wires, filaments, or cords 32 may be manipulated to shape outer margin or rim element 22 in-situ to match the contours of the surface to which the valve will be attached. Guide wires, filaments, or cords 32 are attached to various portions of the outer margin or rim element 22 at spaced points therealong. Guide wires, filaments, or cords 32 are used as manipulators to adjust the shape and position of the scaffold 20, and to hold it in position while the outer margin or rim element 22 is fixed to the adjacent tissue surface.

As schematically represented in FIG. 4, delivery catheter 30 may be inserted into the left atrium 36 from a venous access by crossing the inter-atrial septum 38 from the right atrium 40 to deploy the valve scaffold or support device 20 over the mitral valve 12 (FIG. 3).

FIG. 5 depicts scaffold 20 in an intermediate stage of ejection from delivery catheter 30. At the onset of a percutaneous implantation procedure, when catheter is being manipulated through the vascular system, preferably the venous system, to the heart, scaffold 20 is stored in a collapsed configuration inside a distal end portion of the catheter. Alternatively, the collapsed scaffold may be inserted into a proximal end of the catheter and pushed to the distal end after the arrival of the distal end at the surgical site.

FIG. 5 shows a partially expanded scaffold 20 emerging from the distal end of catheter 30 together with distal ends of a pair of guide wires, filaments, or cords 32. FIG. 6 similarly shows a completely ejected and expanded scaffold 20 outside the distal end of catheter 30 with several guide wires, filaments, or cords 32 extending from the lumen (not designated) of catheter 30 to outer margin or rim element 22.

As depicted in FIGS. 7 and 8, outer margin or rim element 22 may be pre-assembled with fixation elements 34, which engage heart tissue after the scaffold 20 is in position. Fixation elements 34 are spaced sufficiently close to one another to attach outer margin 22 circumferentially to the tissue so as to create a continuous or near continuous contact between the tissue and the scaffold 20. Fixation elements 34 may take any form suitable for achieving this result. Acceptable candidates include hooks, barbs, anchors, and aliquots of adhesive. The adhesive may be initially in an inert form and activated by the application of waveform energy, electromagnetic or ultrasonic, or possible heat energy. Alternatively, fixation may also be achieved using similar means through the membrane adjacent to the outer margin (not depicted). A separate instrument may be inserted into the heart chamber or guided to the surgical site for activating the adhesive.

Once implantation of scaffold or support device 20 has been completed, orifice 28 is ready to receive a circular or cylindrical valve prosthesis 42 (FIG. 9) through the same or another delivery system, though the valve prosthesis could alternatively be surgically implanted.

Annular inner margin or rim element 26 may be either elastic or inelastic with respect to its circumference and may be rounded or irregularly shaped and asymmetric, as appropriate to the valve morphology. In general, the combination of the implantable scaffold or support device 20 and the subsequently placed valve 42 (FIG. 9) will create complete separation between the chamber of fixation (e.g., 36) proximal and distal to the membrane margins, except for flow through the valve.

For purposes of facilitating a surface substantial enough to allow fixation of a valve 42, orifice 28 acting as the neo-annulus may have a cylindrical configuration, creating a surface rather than a rim. The cylindrical surface of the annulus extends perpendicularly to the plane of the membrane portion 24 of the scaffold device 20 and the plane of the native mitral annulus and in alignment with or parallel to the blood flow. The cylinder may be made of metal mesh, inelastic cloth, material elastic in only one plane (the plane of the blood-flow), a coil, inflatable lumen, or other appropriate material.

The cylindrical surface may be an integral part of the implanted scaffold 20, or may be attached by a separate step at some time-point after the scaffold has been deployed. Fixation to the inner margin or annular member 26 may be by compression, hooks, barb, or other appropriate means.

Valve scaffold or support device 20 may be provided with a means of tethering the sub-valvular apparatus into orifice 28 in order to take advantage of any potential contribution of the sub-valvular apparatus to cardiac function.

FIG. 9 depicts valve scaffold or support device 20 with outer conformable margin 22 fixed at the mitral annulus, an abbreviated membranous portion 24 separating the spaces, and cylindrical implanted valve 42 with apposed leaflets in profile resides within the neo-annulus.

Figure 10:
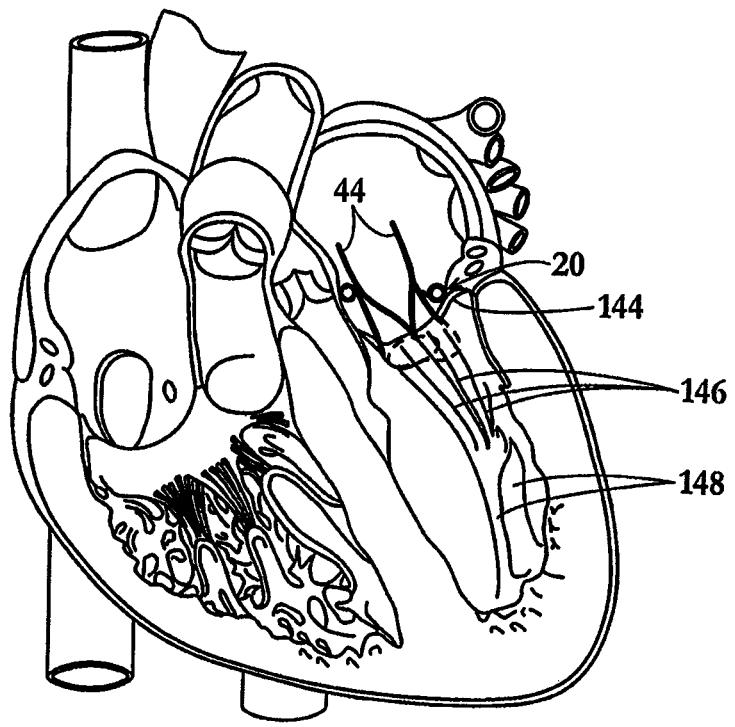
FIG. 10 is a photograph that shows loop tethers surrounding the cords, which in this iteration, are pulled though the neo-annulus so that with subsequent fixation of the valve, papillary function may continue to impact cardiac function.

FIG. 10 is a photograph that shows loop tethers 44 surrounding the cords or cordae tendenae 46 which in this iteration, are pulled though the neo-annulus orifice 28 so that with subsequent insertion and fixation of the valve 42, papillary function may continue to impact cardiac function.

Outer conformable margin 22 may be made of a pliant material, likely tubular in nature, in which fixation elements or fasteners 34 in the form of hooks, barbs, expandable anchors, or other appropriate attachment elements may be held. When the outer conformable margin or rim element 22 is positioned, fixation elements 34 are extended or otherwise deployed into the internal tissues of the atrial wall 18 to cause fixation. Parts of the outer conformable margin 22 may be attached either separately or all at one time. Outer margin 22 may be covered with a porous material such as polyester, or similar biocompatible covering to facilitate tissue in-growth.

Alternatively the fixation elements or fasteners 34 may comprise hooks, barbs, screws, anchors, staples, magnets, glue, stents, or other fixation components that are delivered and deployed in part or totally separately from the implantable valve scaffold itself. Thus, valve scaffold 20 may be initially free of fixation elements or fasteners 34, with the fixation elements being attached in situ to the scaffold and the host tissue surface.

Commercially available valves, as well as those in development for catheter delivery and commercial availability in the future, are generally round, and, in the case of those designed for catheter delivery, are used either trans-arterially or trans-apically in the aortic position, but have not been used for the mitral valve replacement because of the asymmetry of the annulus and native valve. These devices cannot fit within the asymmetrical contours of a heart chamber. However, using scaffold 20, this asymmetrical chamber opening is converted to a round opening, thereby enabling existing round valve designs to be adapted for use in the mitral valve area.

Also, since the left atrium can be accessed through the venous system across the foramen ovale, it will accommodate a larger catheter than can generally be passed through the arterial side, and can address both the tricuspid and the mitral, neither of which now has a strategy for catheter-based replacement.

In general, a significantly larger valve may be required in the mitral position than in the aortic, and the valve 42 may be positioned into the orifice 28 of the neo-annulus by way of catheter 30, and expanded into the orifice. Orifice 28 may be a hole that receives and seats valve 42. Alternatively, orifice 28 may have valve connectors pre-assembled with scaffold 20 prior to placement to facilitate mounting. Alternatively, a standard prosthetic or bio-prosthetic valve may be sewn into place in an open procedure The primary use of scaffold 20 is in the mitral area. However, scaffold 20 may be adapted for use with the tricuspid, with slight modification to allow for the coronary sinus orifice. Of course, scaffold 20 can be adapted for providing a neo-annulus in any location where such a neo-annulus would have therapeutic value. As the membranous portion 24 can vary in size depending on the discrepancy in size between the desired valve and the dimensions of the surrounding tissue to which the scaffold will be fixed, and the outer margin 22 is conformable to virtually any irregular contour opening, it is clear that scaffold 20 is adaptable for location in many areas of the body, and is not limited to the particular embodiments shown and described herein, as would be understood by one skilled in the art.

Figure 11:
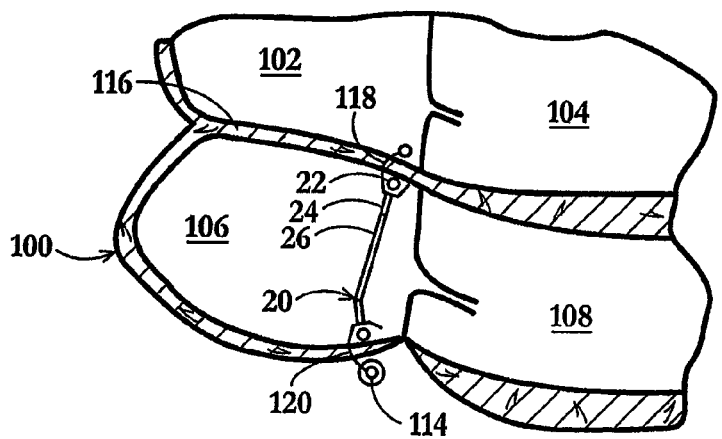
FIG. 11 is a diagram showing a four-chamber view of the heart with the margin of an implantable scaffold in accordance with the present invention fixed through the coronary sinus and the atrial septum.

FIG. 11 diagrammatically depicts a heart having a right atrium 102, a right ventricle 104, a left atrium 106, and a left ventricle 108, with valve scaffold or support platform 20 implanted therein. Outer margin or perimeter element 22 is fixed via fasteners 118 and 120 through the coronary sinus 114 and the atrial septum 116.

Figure 12:
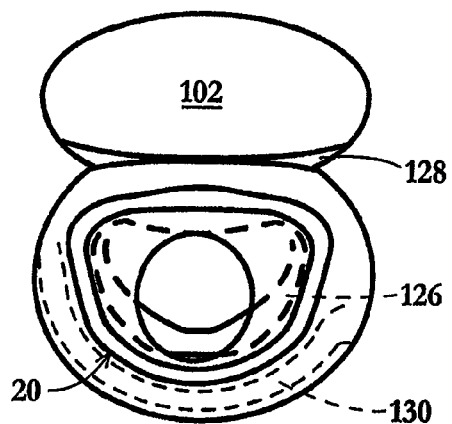
FIG. 12 is a schematic view of the mitral valve and atrial septum from the dome of the atrium. The tricuspid valve is not illustrated. The route of the coronary sinus is shown under the left atrial wall and roughly parallel to the posterior annulus.

FIG. 12 schematically illustrates a mitral valve 126 and atrial septum 128 from the dome of the left atrium 106 (FIG. 11) with scaffold or valve support device 20 in position in the atrium adjacent the mitral valve. The tricuspid valve is not illustrated. The route of the coronary sinus 130 is shown under the left atrial wall and roughly parallel to the posterior annulus.

Figure 13:
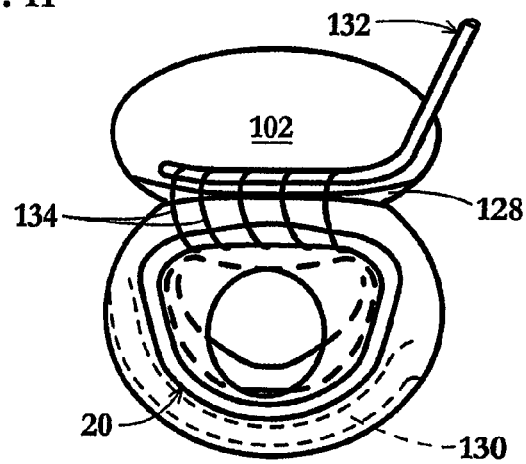
FIG. 13 is a schematic view similar to FIG. 12, illustrating a separate device passed into the right atrium equipped with fixation elements, which can attach to a portion of the margin of the scaffolding for partial anterior fixation.
Figure 14:
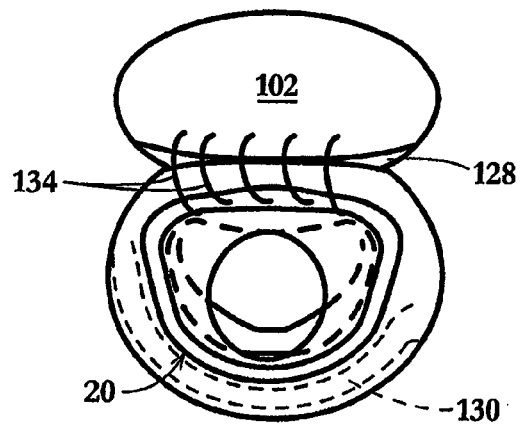
FIG. 14 is a schematic view similar to FIGS. 12 and 13, showing a scaffold is a schematic view similar to FIG. 12 fixed through the atrial septum as a result of the right atrial device used in FIG. 13.

As shown in FIG. 13, a separate device 132 may be passed into the right atrium 106 equipped with fixation elements 134, which can attach to a portion of the outer margin or rim element 22 of scaffold or valve plafform 20 for partial anterior fixation. FIG. 14 shows scaffold or valve platform 20 fixed through the atrial septum 128 as a result of the right atrial device 132 used as depicted in FIG. 13.

Figure 15:
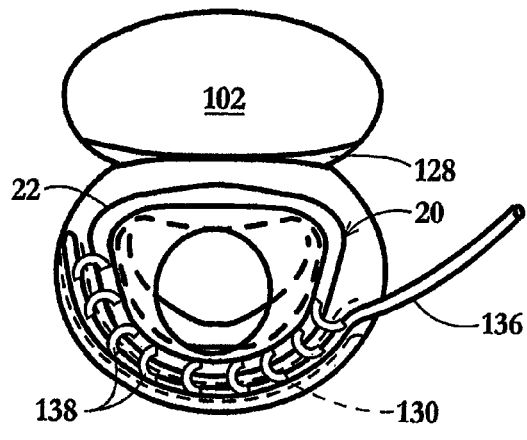
FIG. 15 is a schematic view similar to FIG. 12, illustrating a separate device passed into the coronary sinus equipped with fixation elements, which can attach to the margin of the scaffolding for partial posterior fixation.
Figure 16:
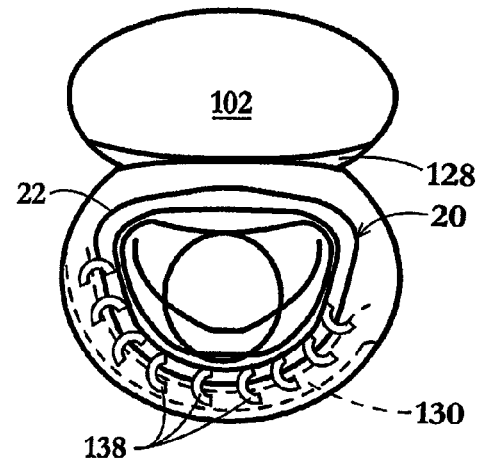
FIG. 16 is a schematic view similar to FIG. 15, showing a scaffold in accordance with the present invention fixed through the atrial wall through the coronary sinus as a result of the coronary sinus device used in FIG. 15.

As illustrated in FIG. 15, another surgical device 136 equipped with fixation elements 138 is passed into the coronary sinus 130. Fixation elements 138 attach to the outer margin or rim element 22 of scaffold or valve support platform 20 for partial posterior fixation. FIG. 16 shows scaffold or valve support platform fixed through the atrial wall via the coronary sinus 130 as a result of the coronary sinus device 136 used as depicted in FIG. 15.

Figure 17:
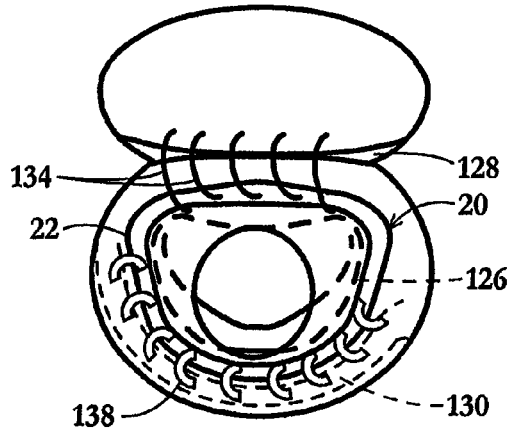
FIG. 17 is a schematic view similar to FIGS. 14 and 16, showing the scaffold fixed through both the atrial septum and the coronary sinus as a result of the right atrial device used in FIG. 13 and the coronary sinus device shown in FIG. 15.

FIG. 17, a schematic view similar to those of FIGS. 14 and 16, shows scaffold or valve support platform 20 secured in position next to the mitral valve 126 (A) by fixation elements or fasteners 134 extending through the atrial septum 128 as a result of the use of the right atrial device 132 pursuant to FIG. 13 and (B) by fixation elements or fasteners 138 extending from the coronary sinus 130 as a result of the use of the coronary sinus device pursuant to FIG. 15.

Figure 18:
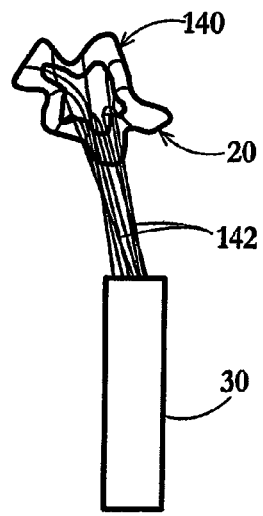
FIG. 18 is a schematic top plan view showing a collapsed valve scaffold device in accordance with the present invention emerging from a distal end of the delivery catheter. In this iteration, a series of tethers or cords attached either to the margin, through the membranous portion, or more centrally, and are used to propel and position the scaffolding into place around the annulus.
Figure 19:
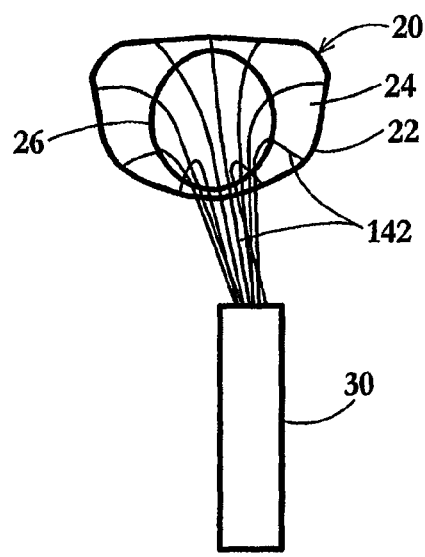
FIG. 19 is a schematic view similar to FIG. 18, showing the expanded implantable valve scaffold maneuvered into position by one or more guiding cords, tethers, guide wires or filaments, which allow advancement or retraction of any portion of the margin of the implantable into apposition with the tissue at the desired location.

FIG. 18 shows a collapsed configuration 140 of valve scaffold or support device 20 emerging from a distal end of delivery catheter 30. In this iteration, a series of tethers, cords, wires or filaments 142 are attached either to outer margin 22, through the membranous portion 24, or more centrally, and are used to propel and position the scaffold or valve support device 20 into place around the annulus. Scaffold 20 expands automatically by virtue of the internal stresses of the shape memory material such as titanium and nitinol of which the scaffold is fabricated. FIG. 19 depicts the expanded implantable valve scaffold 20 maneuvered into position by one or more guiding cords, tethers, wires or filaments 142, which allow advancement or retraction of any portion of the outer margin 22 of the implantable scaffold 20 into apposition with the tissue at the desired location.

Figure 20:
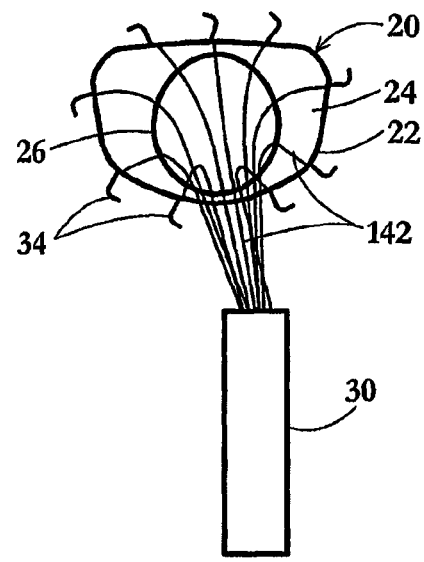
FIG. 20 is a schematic view similar to FIG. 19, showing the guiding cords, tethers, wires or filaments, advanced or else a fixation device at the end of each cord, tether, guide wire or filament is advanced at the margin to perforate the tissue and accomplish fixation. The fixation portion may be a detachable portion of the guides, or a separate element either advanced by or over the guides.
Figure 21:
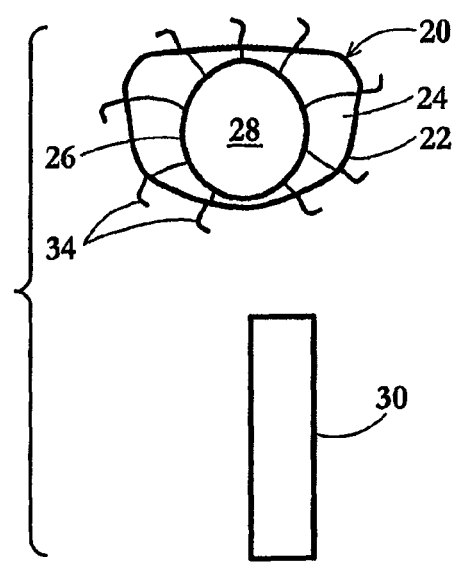
FIG. 21 is a schematic front elevational view of the implantable scaffold of FIGS. 19 and 20, showing the cords as retracted into the catheter so as to leave the deployed, fixed implantable valve scaffold with the neo-annulus located centrally over the native valve (not shown).

FIG. 20 diagrammatically shows the guiding cords, tethers, wires or filaments 142 and a fixation element or fastener 34 at the end of each cord, tether, guide wire or filament advanced at the margin 22 to perforate the tissue and accomplish fixation. Fixation elements or fasteners 34 may be detachable portions of cords, tethers, guide wires or filaments 142, or separate elements advanced either by or over the guides 142. In FIG. 21 cords, tethers, guide wires or filaments 142 have been retracted into the catheter 30 so as to leave the deployed, fixed implantable valve scaffold 20 with the valve-receiving orifice or neo-annulus 28 located centrally over the native valve (not shown).

Figure 22:
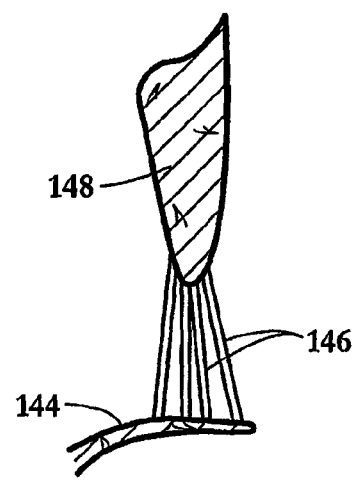
FIG. 22 is a diagram showing the mitral or tricuspid leaflet, with the cords and papillary muscle depicted in a long axis view.

FIG. 22 is a diagram showing a mitral or tricuspid leaflet 144, with the cords or cordae tendenae 146 and papillary muscle 148 depicted in a long axis view.

Figure 23:
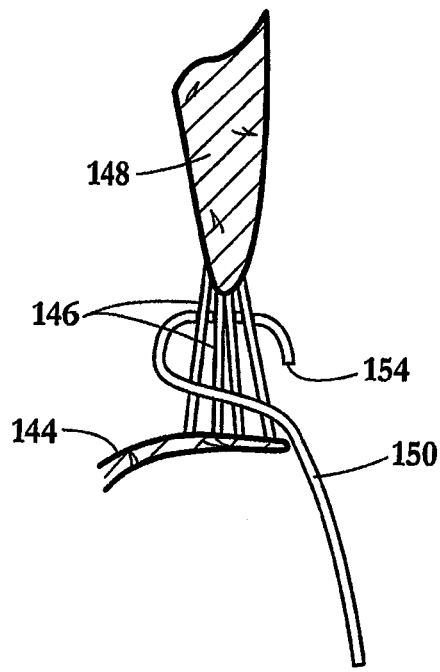
FIG. 23 is a diagram similar to FIG. 22, showing a pre-formed or steerable catheter passed around the cords or papillary muscle. In this view, the catheter is coming from the atrium, but the catheter could alternatively pass through the ventricular wall or ventricular outflow valve.
Figure 24:
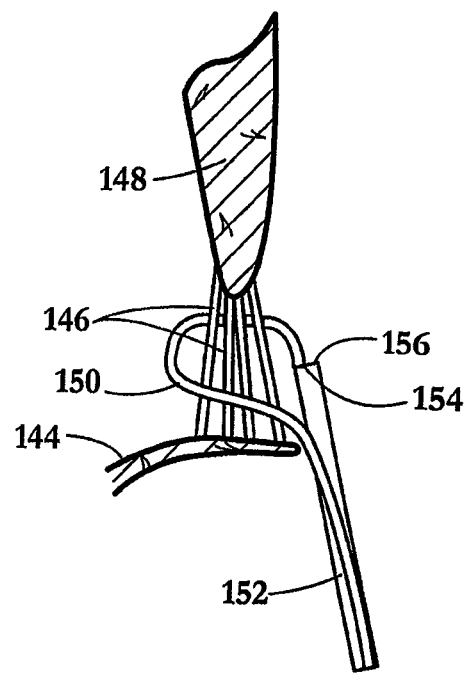
FIG. 24 is a diagram similar to FIGS. 22 and 23, showing a second, sliding catheter passed over or adjacent to the shaft of the first catheter, or by some other route or guidance system, such that the open distal ends of the two catheters appose, creating a continuous lumen.

As shown in FIG. 23, a pre-formed or steerable catheter 150 is passed around the cords 146 and/or papillary muscle 148. In this view, catheter 150 extends from the atrium 102 or 106 (FIG. 11), but the catheter could alternatively pass through the ventricular wall or ventricular outflow valve. As shown in FIG. 24, a second, sliding catheter 152 is passed over or adjacent to the shaft of the first catheter 150, or by some other route or guidance system, such that open distal ends 154 and 156 of the two catheters appose, creating a continuous lumen.

Figure 25:
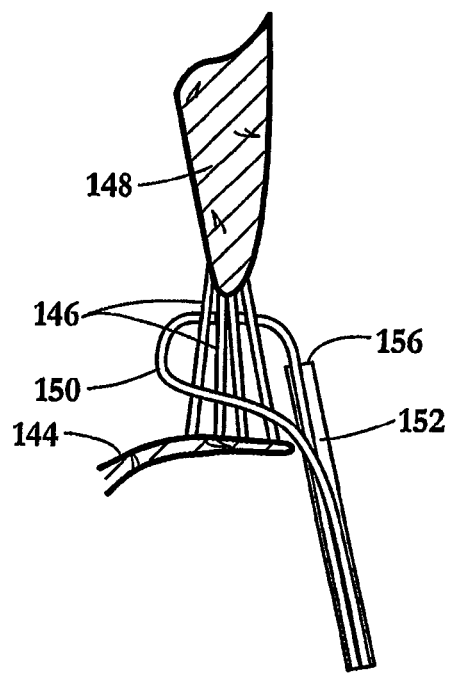
FIG. 25 is a diagram similar to FIGS. 22-24, showing a continuous tether passed through the looping and sliding catheters, retrieved out the proximal ends of the catheters.
Figure 26:
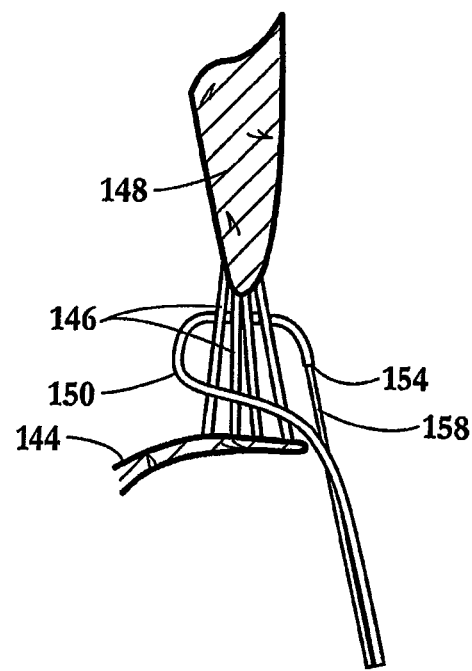
FIG. 26 is a diagram similar to FIGS. 22-25, showing that the second, sliding catheter has been removed revealing one part of the tether surrounding the cords
Figure 27:
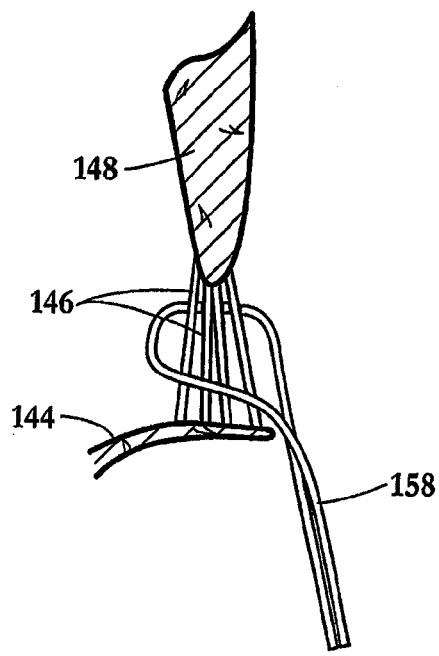
FIG. 27 is a diagram similar to FIGS. 22-26, showing that the preformed or steerable catheter, which previously surrounded the sub-valvular apparatus, has been removed revealing the free tether surrounding the cords, available for incorporation into the scaffold or valve.

Pursuant to FIG. 25 a continuous tether 158 is passed through looping catheter 150 and sliding catheter 152, via their apposed distal ends 154 and 156, and extends out the proximal ends (not shown) of the catheters. In FIG. 26 sliding catheter 152 has been removed, revealing one part of tether 158 surrounding the cords 146. In FIG. 27 preformed or steerable catheter 150, which previously surrounded the sub-valvular apparatus 146, 148, has been removed, revealing tether 158 free and surrounding the cords 146, available for incorporation into scaffold 20 or valve 42 (FIG. 9). Pursuant to one option, tether 158 extends through orifice or neo-annulus opening 28 prior to the seating of the prosthetic or bio-prosthetic valve 42. Upon the seating of valve 42, tether 158 is pinched or clamped between inner margin or rim element 26 (see, e.g., FIG. 2) and the seated valve.

The tethering of scaffold 20 and valve 42 to the subvalvular apparatus, i.e., cords 146 and/or papillary muscle 148, serves in part to anchor the implanted devices 20 and 42 in position in opposition to the pressure exerted during ventricular systole. In addition, the anchoring preserves the natural distribution of stresses throughout the heart and accordingly reduces the likelihood of cardiac failure owing to an imbalance in the forces affecting the heart muscles.

Figure 28:
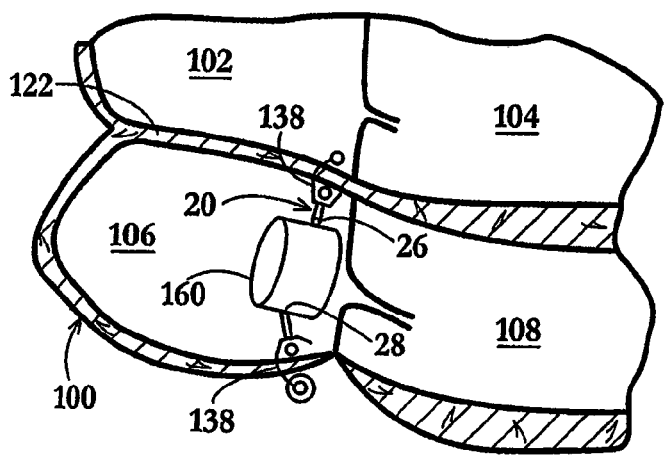
FIG. 28 is a diagram showing a four-chamber view of the heart with a cylindrical sheath, framework, or other support added at a neo-annulus of an implantable scaffold in accordance with the present invention to act as a landing zone for a subsequently placed valve

FIG. 28 is a diagram similar to FIG. 11 and utilizes the same reference designations for corresponding structures. As depicted in FIG. 28, a cylindrical sheath, framework, or other support 160 is inserted into a neo-annulus orifice 28 of scaffold 20 to act as a landing zone for a subsequently placed prosthetic or bio-prosthetic valve (not shown). Tether 158 may be clamped between orifice margin or rim element 26 and cylindrical sheath, framework, or support 160. Sheath, framework, or support 160 provides increased surface area for attachment of an off-the-shelf valve and may be provided with fasteners (not shown) to securely link to margin or rim element 26.

Figure 29:
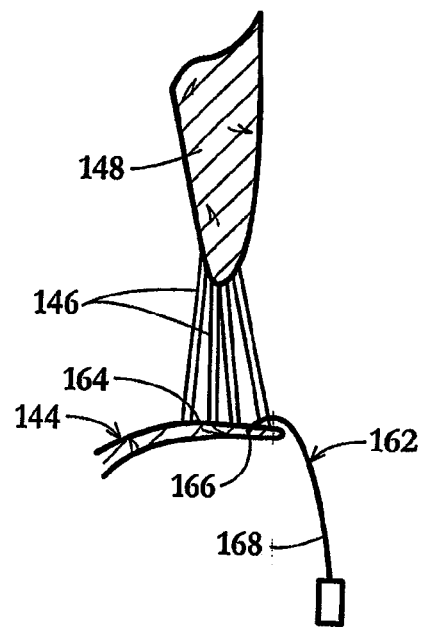
FIG. 29 is a diagram similar to FIG. 22 but showing an alternative embodiment for capture of the sub-valvular apparatus where an element is delivered to the underside of the valve leaflet (shown as a single barb on a single leaflet), to engage the valve on or near the attachment of the cordae, allowing an extension of the barb to attach to the scaffolding or neo-annulus allowing transmission of papillary systolic forces to the valve.

FIG. 29 shows an alternative embodiment for capture of the sub-valvular apparatus, including cordae tendenae 146 and papillary muscle 148, where a fastening element 162 is delivered to the underside 164 of valve leaflet 144 (shown as a single barb on a single leaflet), to engage the mitral valve on or near the attachment of the cordae. Fastening element 164 may take the form of a hook or barb 166 at the end of a tether 168. The hook or barb 166 is inserted into the tissue of the leaflet 144 and secured thereto along underside 164 or to cordal junctions. Tether 168 is left in place for incorporation into scaffold 20 or anchoring to the scaffold and the prosthetic valve, allowing transmission of papillary systolic forces to the valve.

Figure 30:
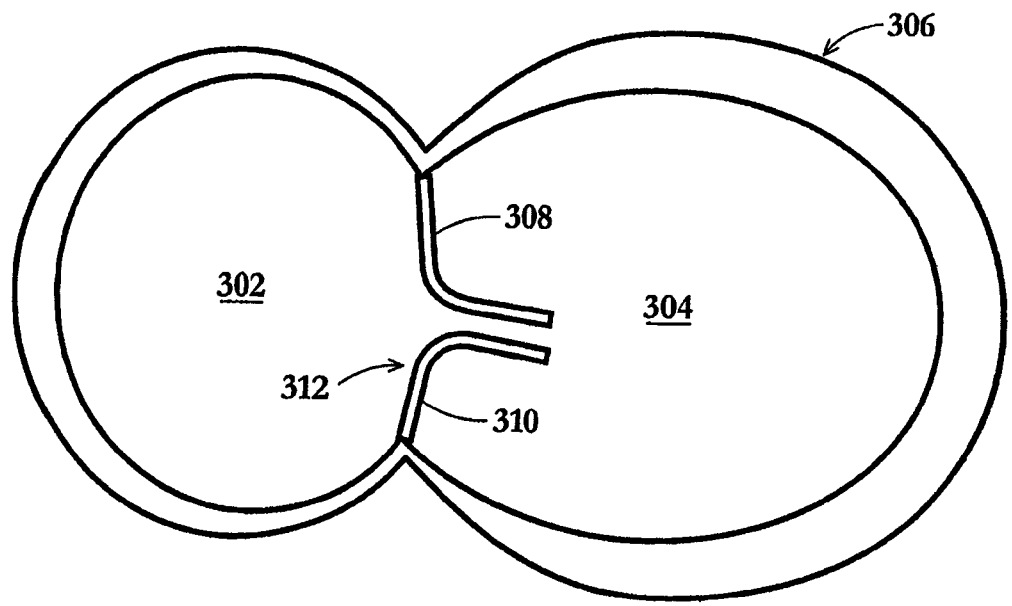
FIG. 30 is a schematic cross-sectional view of the left atrium and left ventricle of a heart, showing mitral valve leaflets in a nearly closed configuration.
Figure 31:
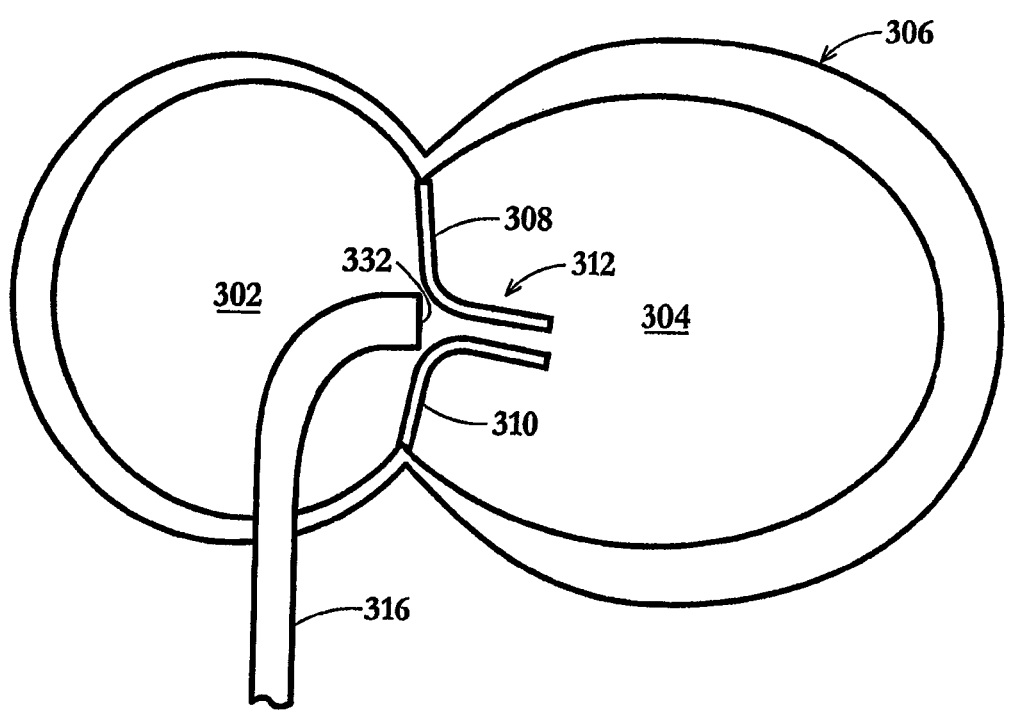
FIG. 31 is a schematic view similar to FIG. 29, showing a delivery catheter passed across the inter-atrial septum from the right atrium into the left atrium.

FIGS. 30 through 36 represent successive stages of a procedure for implanting an alternative valve scaffold 300 in accordance with principles delineated herein. FIG. 30 depicts a left atrium 302 and left ventricle 304 of a heart 306, showing leaflets 308 and 310 of a mitral valve 312 in a partially closed configuration representing a malfunctioning of the mitral valve. In a procedure deploying a prosthetic valve 314 (FIG. 36) to effectively replace the mitral valve 312, a delivery catheter 316 is passed across the inter-atrial septum 318 from the right atrium 320 into the left atrium 302, as shown in FIG. 31.

A distal end portion of catheter 316 carries valve scaffold or mounting platform 300 in a collapsed configuration (not shown). As described hereinafter with reference to FIGS. 32-34, the scaffold or platform 300 is ejected and expanded in stages to displace leaflets 308 and 310 outwardly, to fold or curl the leaflets into a more compact configuration and to attach the scaffold or frame to the leaflets. Scaffold 300 is made of at least one shape memory material so that the expansion and reconfiguration of the scaffold occurs automatically in response to the ejection of the scaffold from a distal tip 322 of catheter 316.

Figure 32:
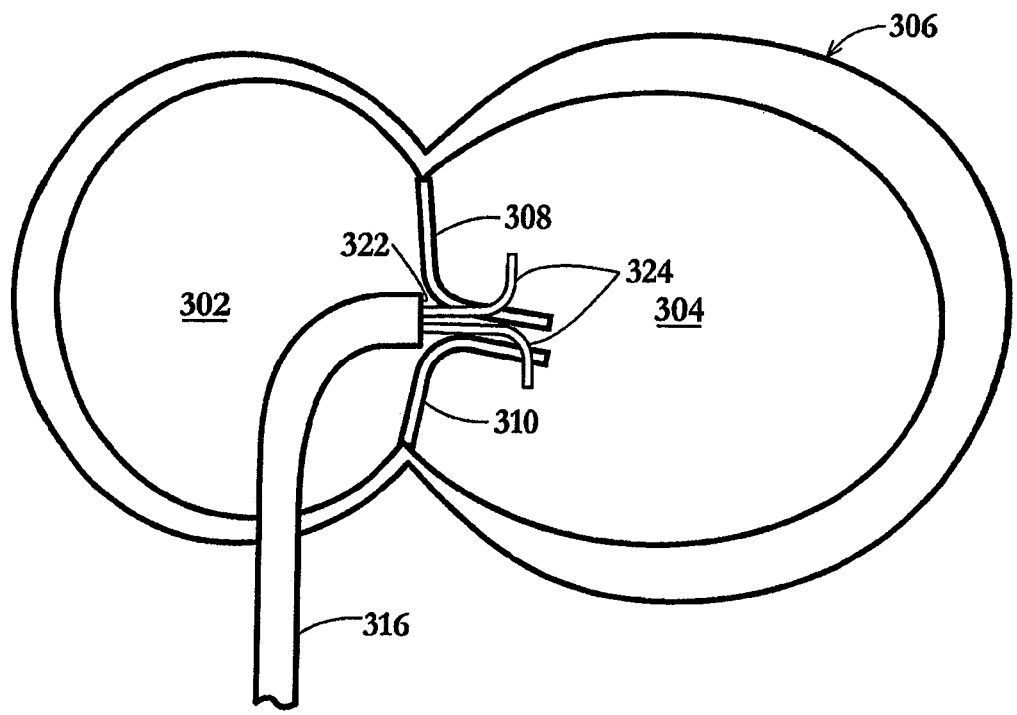
FIG. 32 is a schematic view similar to FIG. 30, showing an early stage of an implantation procedure wherein expanding ventricular fixation hooks of a collapsed valve-seating scaffold in accordance with another embodiment of the present invention extend out of a distal end of the delivery catheter of FIG. 30.
Figure 33:
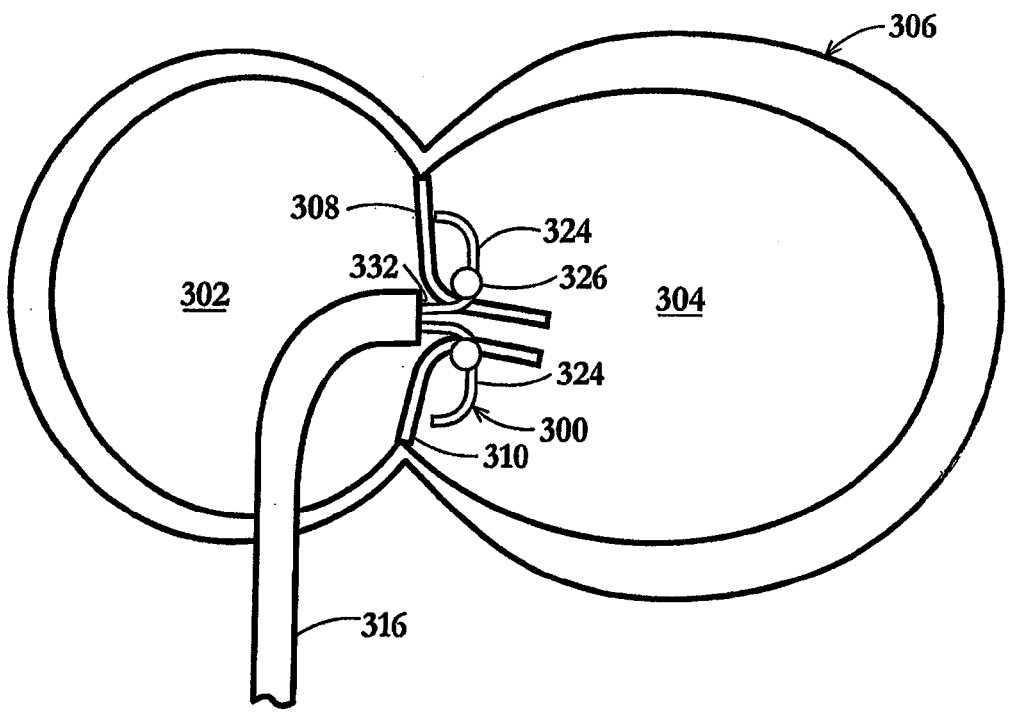
FIG. 33 is a schematic view similar to FIG. 31, showing an intermediate stage of an implantation procedure wherein a partially expanded annular member of the scaffold is disposed generally between the mitral valve leaflets and wherein the ventricular fixation hooks of FIG. 31 extend from the annular member behind the mitral valve leaflets.
Figure 34:
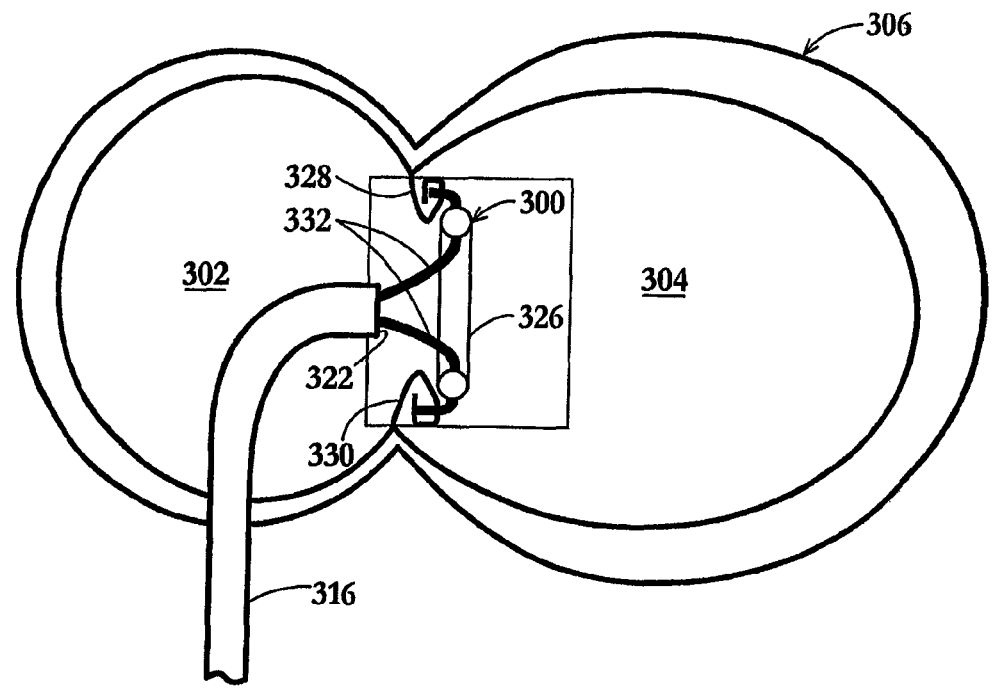
FIG. 34 is a schematic view similar to FIG. 32, showing a later intermediate stage of the implantation procedure wherein the annular member of the scaffold is further expanded and the mitral valve leaflets are folded or curled into a compact configuration and wherein the ventricular fixation hooks of FIGS. 31 and 32 are attached to the mitral valve leaflets.
Figure 37:
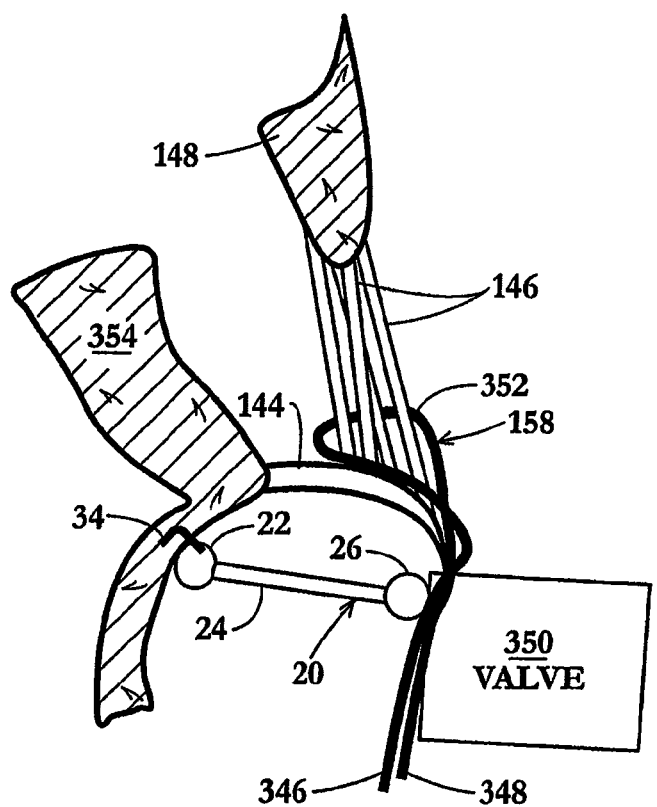
FIG. 37 is a diagram similar to FIG. 27, showing the two-strand tether surrounding the cords, inserted between the scaffold and valve.

After a maneuvering of catheter 315 so that distal tip 322 thereof is juxtaposed to mitral valve 312, as depicted in FIG. 32, the collapsed scaffold or valve-mounting platform 300 is pushed in the distal direction relative to catheter 316 so that a plurality of ventricular fixation hooks 324 of the scaffold emerge from the distal tip of the catheter and insert between the valve leaflets 308 and 310. Upon continued ejection of the collapsed scaffold 300 from catheter tip 322, an annular member 326 of the scaffold emerges into the gap between leaflets 308 and 310, as shown in FIG. 33. The ejected annular member 326 automatically expands thereby folding leaflets 308 and 310 outwardly into curled configurations 328 and 330, as illustrated in FIG. 34. During or immediately prior to this expansion of annular member 326, ventricular fixation hooks 324 pivot towards the curling or folding leaflets 308 and 310 and insert their distal tips between the cordae tendenae into the mitral valve tissues, thus attaching annular member 326 to the mitral valve leaflets 308 and 310 on the ventricular side thereof. FIG. 37 further illustrates an emergence, from catheter tip 322, of a plurality of atrial fixation hooks 332 that are connected to annular member 326. The distended atrial fixation hooks, 332, to the extent that they are still entrained by friction forces to the delivery catheter 316, may be used to fine tune the positioning of the scaffold 300 by maneuvering catheter 316 to exert displacement forces on the scaffold via the extended and deformed atrial fixation hooks.

Figure 35:
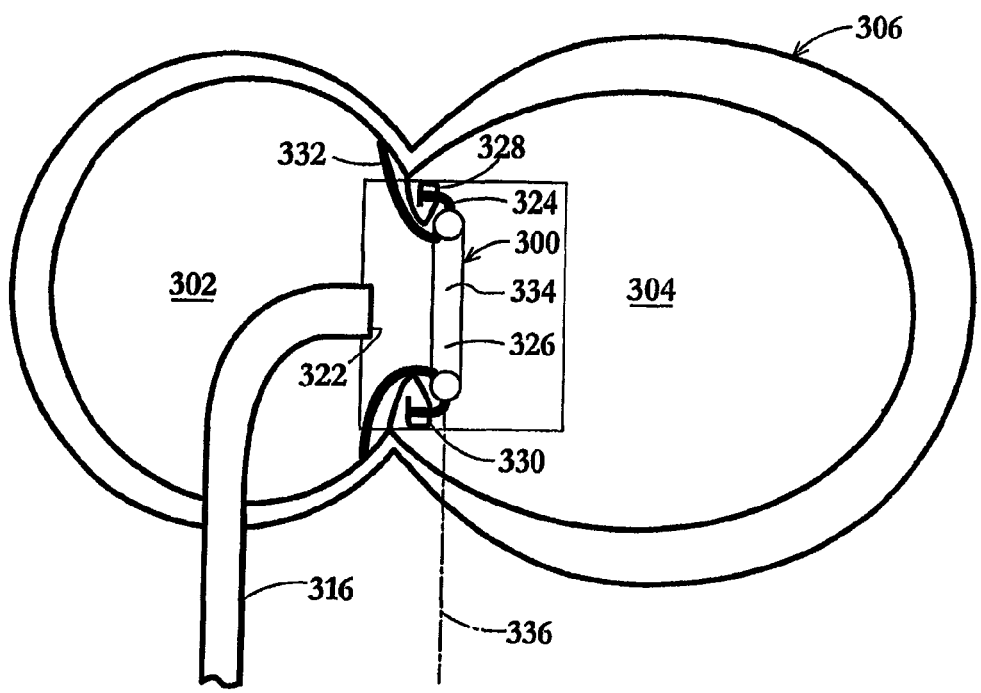
FIG. 35 is a schematic view similar to FIG. 34, showing in a still later intermediate stage of the implantation procedure wherein the scaffold is completely ejected from the delivery catheter and wherein now deployed atrial fixation hooks are extend from the annular member into the atrial chamber and are connected to the mitral valve leaflets.

FIG. 35 shows a late stage of an the implantation procedure wherein scaffold 300 is completely ejected from delivery catheter 316 and wherein atrial fixation hooks 332 have been completely ejected from catheter 317 so that the hooks can assume a predetermined clamping or attachment orientation with distal tips of the hooks inserted into the atrial or mitral-valve tissues on the atrial side of the folded or curled configurations 328 and 330 of the mitral valve leaflets 308 and 310.

Figure 36:
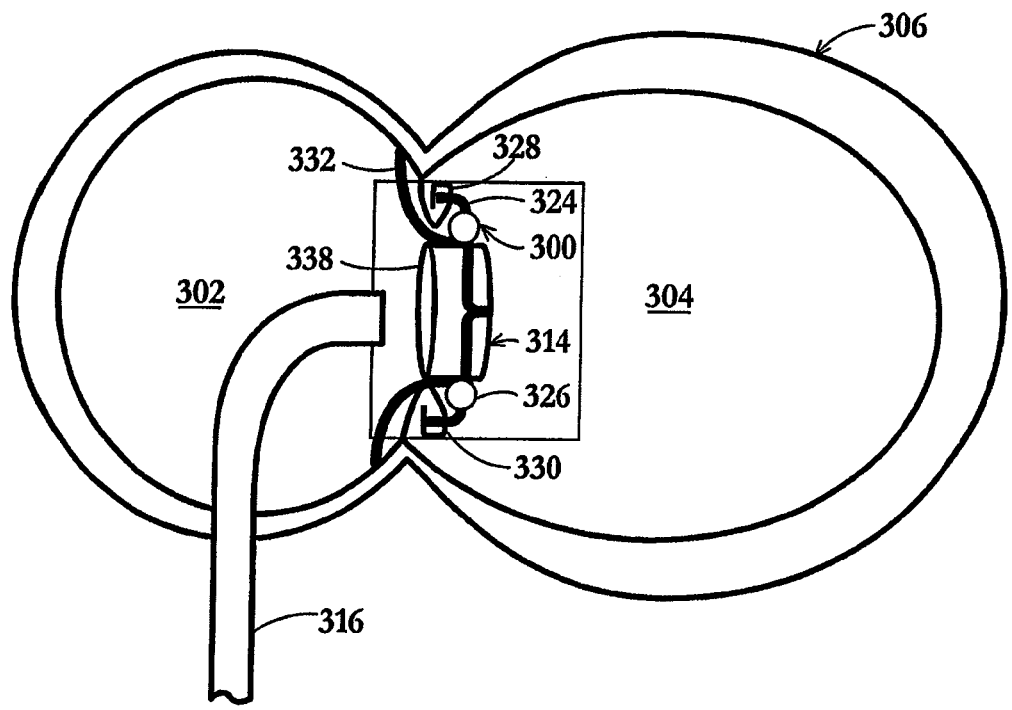
FIG. 36 is a schematic view similar to FIG. 35, showing terminal stage of the implantation procedure wherein a prosthetic valve is seated in the orifice of the valve scaffold.

Annular member 326 of scaffold 300 defines a neo-annulus orifice 334 for receiving or seating prosthetic or bio-prosthetic valve 314 (FIG. 36). Ventricular fixation hooks 324 and atrial fixation hooks 332 are fasteners connected at least indirectly to the annular member for attaching the same all around an outer margin thereof to an tissue surface in the left atrium 302 and to a tissue surface in the left ventricle 304. The tissue surfaces may belong to the atrial leaflets or to the heart chamber walls.

Annular member 326 has a transverse dimension or thickness extending perpendicularly to a major plane 336 (FIG. 35) of the annular member. Ventricular hooks or fasteners 324 extend from the annular member 326 outwardly to one side of plane 336, towards the ventricle 304, while atrial fixation hooks or fasteners 332 extend from the annular member outwardly to an opposite side of plane 336, towards the left atrium 302. Hooks or fasteners 324 and 332 define a space therebetween for receiving and constraining curled configurations 328 and 330 of leaflets 308 and 310.

Annular member 326 and hooks or fasteners 324 and 332 are sized and configured to so constrain the curled configurations 328 and 330 of mitral valve leaflets 308 and 310 that a satisfactory liquid tight seal is created between the curled or folded leaflets and the scaffold 300. Hooks or fasteners 324 and 332 are each made of a shape memory material such as Nitinol, while annular member 326 is made of the same or a different shape memory material such as braided titanium.

When the implantable scaffold 3s disposed in a collapsed delivery configuration inside the distal end portion of delivery catheter 316, the annular member 326 assumes an elongate squashed shape such as that assumed by a collapsed rubber band. The shape memory material of annular member 326 is flexible but not elastic. Annular member 326 is substantially rigid in the finally expanded configuration wherein neo-annulus orifice 334 is sized to seat prosthetic or bio-prosthetic valve 314 in a liquid tight fit.

FIG. 36 depicts a terminal stage of the implantation procedure wherein leaflets 308 and 310 and mitral valve cords (not shown) are fixed to annular member 326 and wherein prosthetic or bio-prosthetic valve 314 is seated in orifice 334 of the valve scaffold 300. Annular member 326 may be provided with an annular lip or ridge (not shown)

which is received in a groove (not shown) on a external wall 338 of valve 314, to enhance of implement formation of a liquid-tight seal.

Hooks or fasteners 324 and 332 are circumferentially spaced about the annular member 326 with an inter-hook spacing of 1-3 mm. Hooks or fasteners 324 and 332 may take any form suitable for attachment to ventricular, mitral valve and atrial tissues. The fasteners 324 and 332 may be barbs, anchors, claws, or clips instead of or in addition to hooks.

It is contemplated that hooks or fasteners 324 and 332 are pre-connected to annular member 326 during the manufacturing process at the factory. However, it is possible for one or more hooks 324 and/or 332 to be attached to annular member 326 in situ, as a step of the implantation procedure. It is contemplated that the procedure of FIGS. 30-36 is percutaneous. However, essentially the same procedure may be conducted via open heart surgery in appropriate cases.

FIG. 37 shows two strands 346 and 348 of the tether 158 of FIG. 27 extending between the inner margin or rim element 26 of scaffold 20 and a prosthetic valve 350. The procedure of FIGS. 22-27 represents one of several ways of anchoring the subvalvular apparatus (cords or cordae tendenae 146 and papillary muscle 148) to the scaffold 20 and valve 350. Tether 158 forms a noose 352 that is passed around cords 146. There are three kinds of cords: primary and secondary, which come off the papillary muscles, and tertiary, which come off the wall 354 of the left ventricle. Noose 352 can capture at least most, if not all, of the primary cords and probably most of the secondary cords. Strands or segments 346 and 348 of tether 158 are placed under tension as valve 350 is seated in orifice or neoannulus 28 and with echocardiographic monitoring, the tension may be adjusted until the systolic shortening caused by the cords pull on scaffold 20.

As depicted in FIG. 38, a fastener 356 may be advanced over both strands or segments 346 and 348 of tether 158 to secure the tether in position relative to the scaffold 20 and valve 350. Fastener 356 acts to compress or clamp the tether strands 346 and 348 at the site of contact with scaffold 20 or more particularly inner margin or rim element 26, acting like a nut of a bolt, so that the fastener, by virtue of its size, holds the noose strands of segments 346 and 348 against the scaffold. Fastener 356 may be coated with material that is blood compatible. Strands or tether segments 346 and 348 are severed at fastener 356 with an end-cutting device (not shown).

Figure 41:
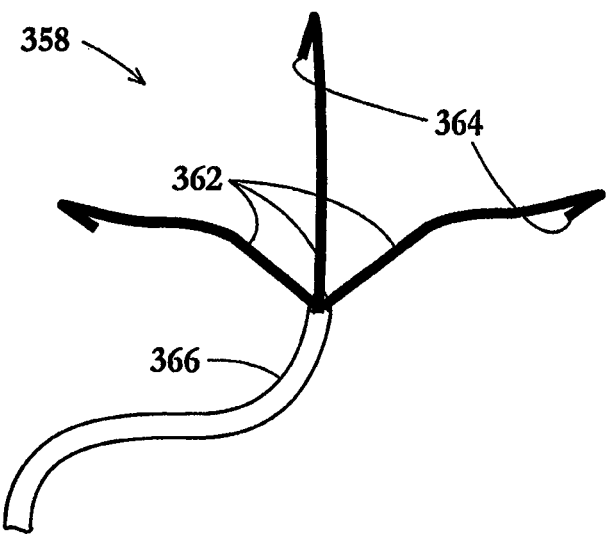
FIG. 41 is a top plan view of the grappling hook of FIGS. 39 and 40.

FIGS. 39-41 show a grappling hook device 358 that forms a particular embodiment of the fastening element 162 described hereinabove with reference to FIG. 29. Hook device 358 includes a stem 360 from which emanate three prongs or fingers 362 each provided at a free end with a hook or barb 364. FIGS. 39-41 depict hook device 358 in an expanded use configuration wherein prongs or fingers 362 are each generally C-shaped and are disposed in respective planes (see FIG. 41) oriented at an angle of about 30° to 60° relative to each other. A tension member or tether 366 is connected to stem 360.

Stem 360 and prongs or fingers 362 are made of a shape memory material such as nitinol, so that hook device 358 may be delivered in a collapsed configuration to an atrial site through a small diameter catheter and deployed through the orifice or neoannulus 28 of scaffold 20.

Figure 42:
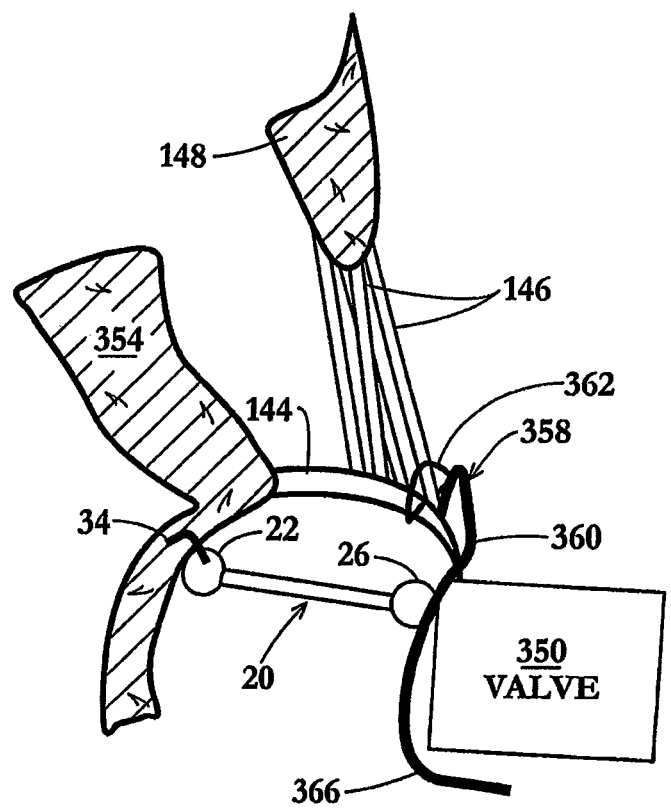
FIG. 42 is a schematic view similar to FIG. 37, showing use of the grappling hook of FIGS. 39-41 in an implantation procedure as described below with reference to FIG. 29.
Figure 43:
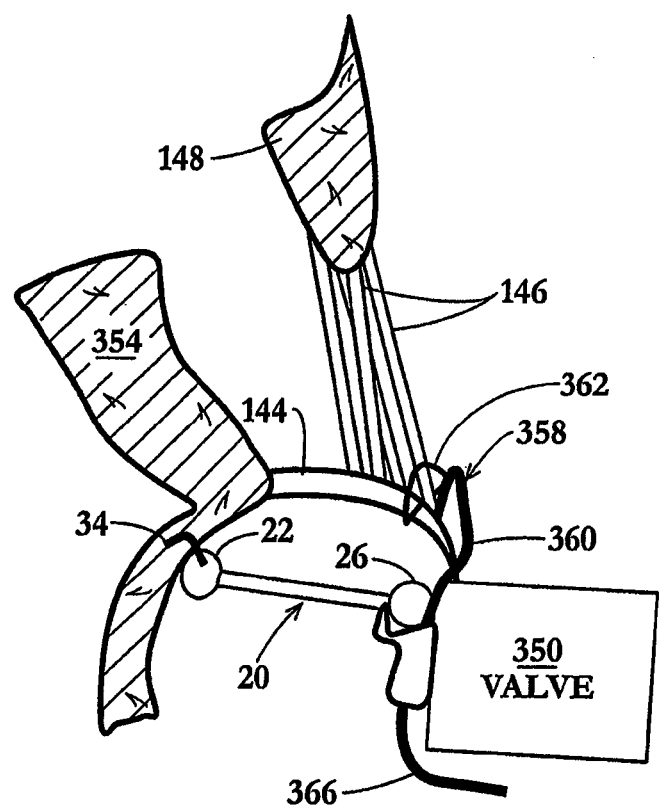
FIG. 43 is a diagram similar to FIG. 42, showing a fastener or locking element crimped to a tether or tension member of the grappling hook of FIGS. 39-42.
Figure 44:
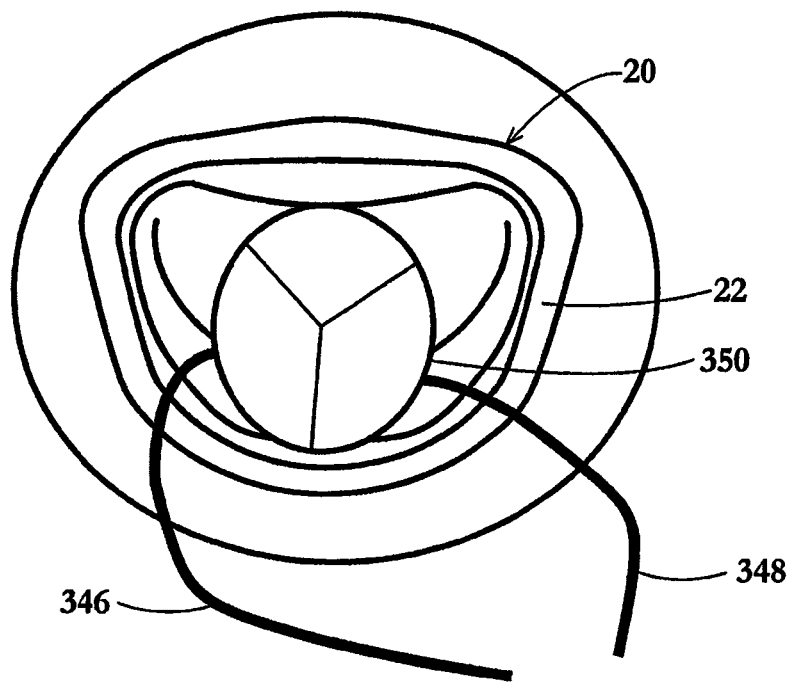
FIG. 44 is a view from the left atrium towards the mitral valve, showing an implantable scaffold in accordance with the present invention fixed in position over a mitral valve and further showing two flexible tension members or tethers extending between the scaffold and a prosthetic valve inserted into the scaffold.

FIG. 42 shows grappling hook device 358 deployed so that barbs 364 at the ends of prongs or fingers 262 engage the edges of mitral valve leaflet 144. Grappling hook 359 engages leaflet 144 and retracts it to orifice or neoannulus 28 (se FIG. 2). Whereas the method of FIGS. 22-27, 37 and 38 transmits papillary forces by enveloping cords 146, the use of grappling hook device 358 pulls on the leaflets 144, which in turn, capture the cords 146. The mechanism of incorporation of the tension member or tether 366 into the combined scaffold 20 and valve 350 is identical to that described above with reference to FIGS. 22-27, 37 and 38, except there is only one tension member 366 per hook device 358, as opposed to the two strands or tether segments 346 and 348 associated with noose 352. As depicted in FIG. 43, a fastener 368 is advanced over tension member 366 of each hook device 358 deployed and the tension adjusted, then fixed. Tension member 366 is severed at fastener 368 with an end-cutting device (not shown). Fasteners 356 and 368 may be crimped to ensure a tight locking engagement with strands or tether segments 346, 348 or tether 366, respectively.

Figure 45:
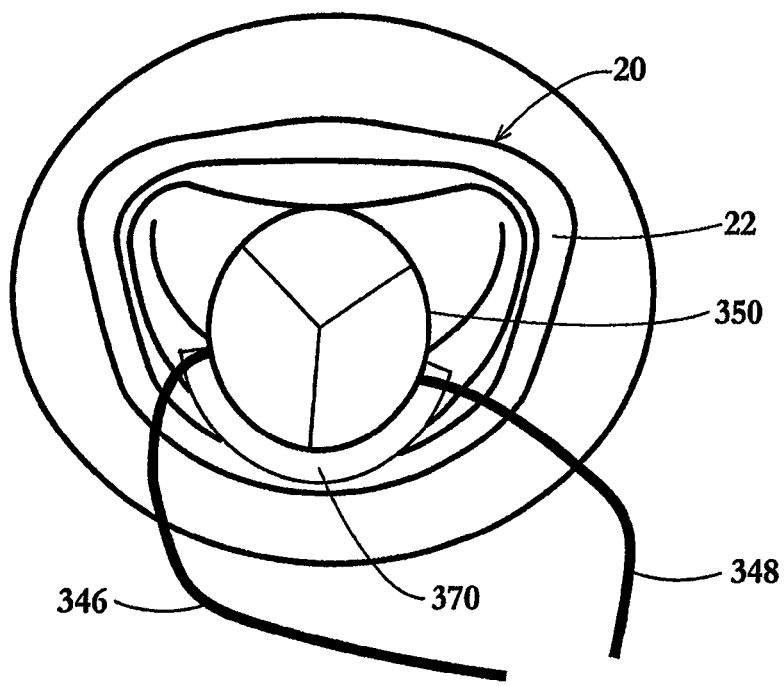
FIG. 45 is a view similar to FIG. 44, showing a spacer extending between the two tension members or tethers.

As an alternative to fastener 356 of FIG. 38, FIG. 45 depicts a spacer member 370 that separates and connects strands or tether segments 346 and 348 associated with noose 352. Spacer member 370 is arc shaped, to fit snugly around cylindrically shaped valve 350 over a portion of inner margin or rim element 26. Strands or tether segments 346 and 348 are disposed with one toward one end of leaflet 144 and the other toward an opposite end. The use of spacer member 370 has the benefit of not foreshortening the leaflet 144.

Figure 46:
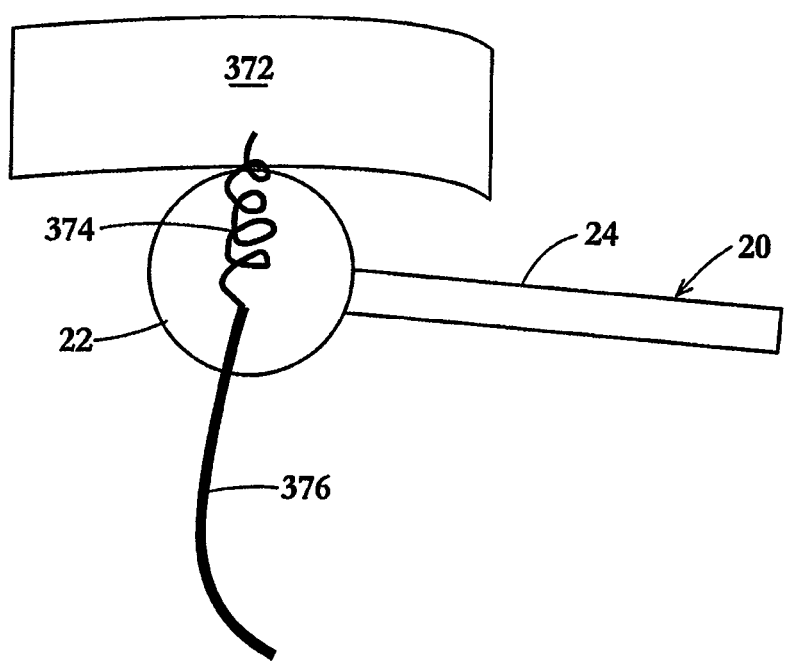
FIG. 46 is a schematic partial side elevational view of a valve-receiving scaffold in accordance with the present invention and a means of attaching the scaffold to a heart wall.

As illustrated in FIG. 46, outer margin or rim element 22 of scaffold 20 may be attached to the heart wall 372 by means of a helical coil element or cork screw 374 that advances into the heart wall upon a twisting of a positioning line 376 that is removably connected to a rear end of the coil or cork screw element.

Figure 47:
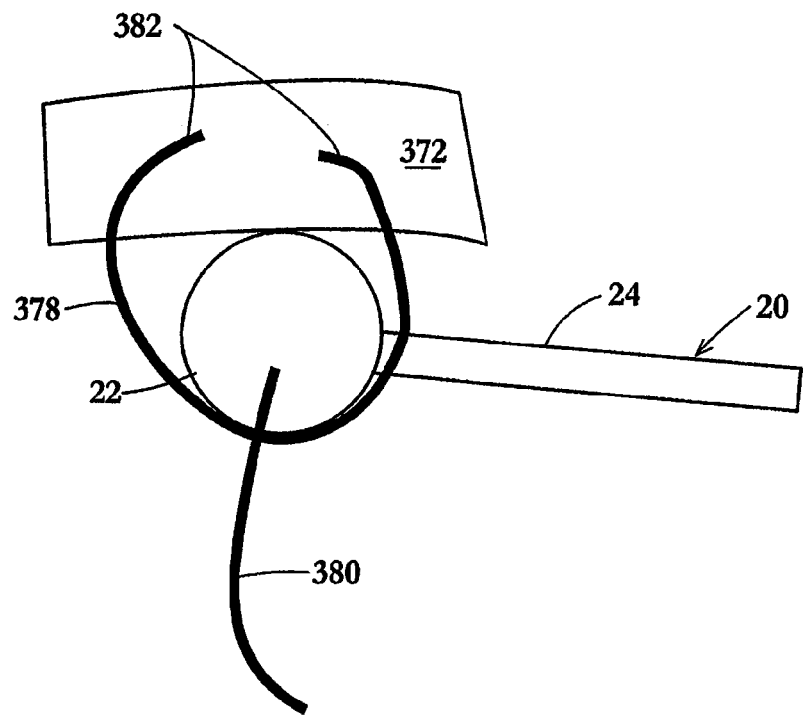
FIG. 47 is a view similar to FIG. 46, showing an alternative means of attaching the scaffold to a heart wall.
Figure 48:
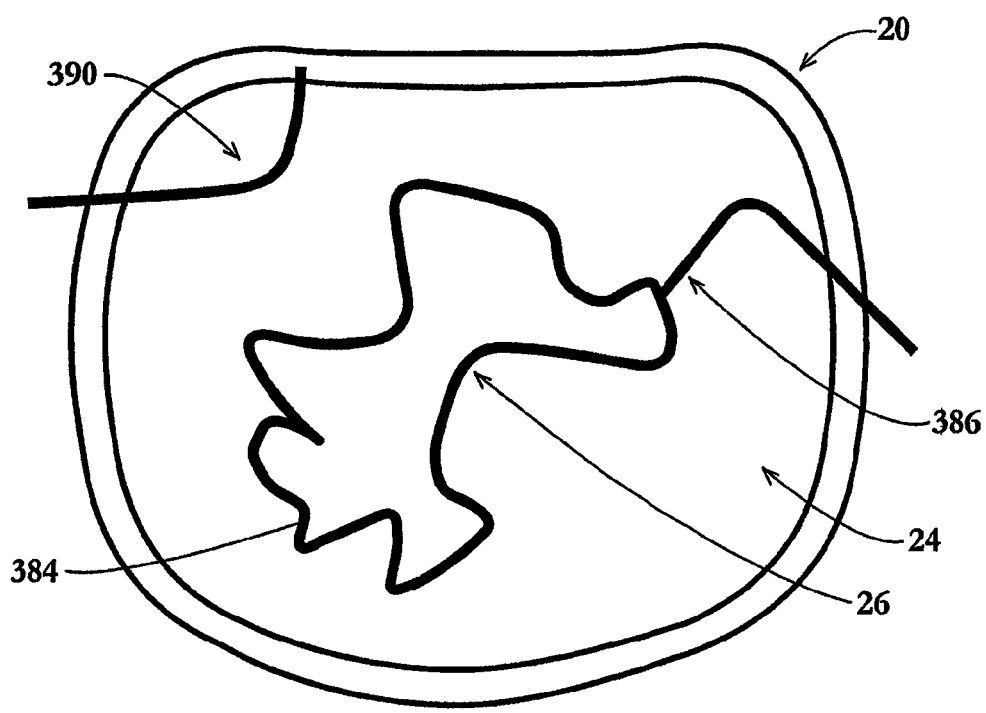
FIG. 48 is a front elevational view of a scaffold or valve-support implant in accordance with the present invention, showing the implant in a partially collapsed configuration.

As shown in FIG. 47, outer margin or rim element 22 of scaffold 20 may be attached to the heart wall 372 by means of a staple 378 that is advanced over a positioning line or wire 380 and around margin or rim element 22 so that leg ends 382 of the staple are inserted into the heart wall. Staple 378 is then pinched, for instance, by a tubular member (not shown) inserted over positioning line or wire 380 and over a rear end of the staple, As depicted in FIG. 48, inner margin or rim element 26 of scaffold 20 may take the form of an annular tubular member with an enclosed lumen (like a non-distensible inner-tube). This annular tubular member 26 is inserted in a collapsed configuration via the delivery catheter (or otherwise in an open heart procedure). After ejection of the scaffold 20 from the distal end of the delivery catheter, the annular tubular member is expanded from a collapsed configuration 384 to a donut (toroidal) shape as in FIG. 2 et seq. by infusion of a liquid through a tube 386 communicating with the lumen of the tubular outer margin or rim element 22. The tubular member is inflatable but not expandable (i.e., is made of inelastic film material), so that valve 42 may be subsequently expanded into orifice or neo-annulus opening 28. In one iteration or embodiment of this approach, if a particular expanded configuration is found to be satisfactory, the inflation fluid could be replaced with another fluid via tube 386 or another tube (not shown) that would congeal into a solid or semi-solid, either by drainage and replacement with a different liquid, or addition of a second liquid, which, when mixed, caused the composite liquid to harden in the lumen and become solid or semi-solid.

The cross-section of the inflatable lumen described above may be circular, or possibly oval with a long axis 388 (FIG.

49) oriented perpendicularly to membranous portion 24 of scaffold 20, thus providing a more cylindrical configuration to the neo-annulus.

Figure 49:
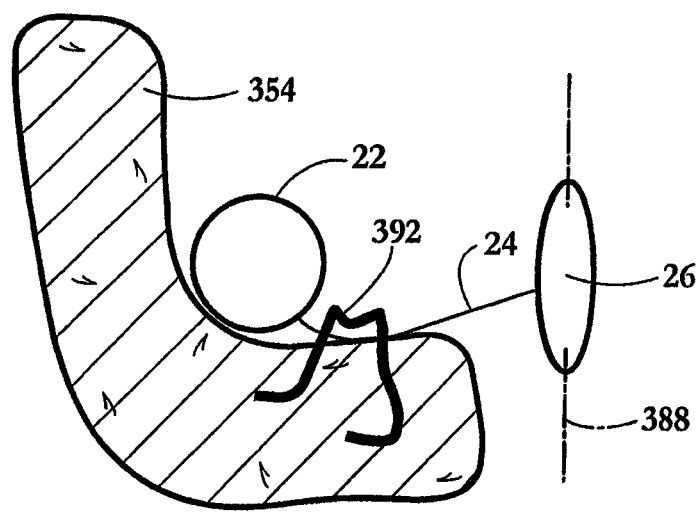
FIG. 49 is a partial cross-sectional view of a heart wall and a partial side elevational view of an embodiment of a valve-support scaffold in accordance with the invention, showing an alternative method of attachment of the latter to the heart wall, pursuant to the invention.

Additionally or alternatively, outer margin or rim element 22 of scaffold 20 may take the form of an inflatable tubular member with an annular lumen inflatable by virtue of a removable tube 390 (FIG. 48), as described above for the inner margin or neo-annulus rim element 26. In this instance, the material of the tubular member may be rigid, but more likely semi-soft, allowing a tight fit with the heart wall. In this iteration, it may be necessary to fix the outer margin 26 to the heart wall indirectly by through and through staples, hooks, or barbs 392 (FIG. 49) at the adjacent edge of the membrane 24, rather than directly through the margin 26.

Alternatively, the lumen of the margin may contain a substance which is hydrophilic, such that it expands automatically when in contact with serum/blood/plasma. This may apply also to the neo-annulus.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A device or assembly for use in heart valve placement in a subject, the device or assembly comprising an implantable scaffold including:
   an inner margin element defining an orifice for receiving or seating a prosthetic or bio-prosthetic valve; and
   a flexible outer margin element conformable to an irregular internal wall surface of a heart chamber, said outer margin element surrounding said inner margin element, said outer margin element and said inner margin element being different from one another and spaced in their entireties from one another, said outer margin element and said inner margin element being coplanar substantially in their entireties with one another, the device or assembly further comprising a placement and positioning mechanism engageable with said scaffold and particularly said outer margin element for conforming said outer margin element to an irregularly shaped tissue surface, said placement and positioning mechanism including a plurality of manipulator tethers or wires extending to said outer margin element, said manipulator tethers or wires being detachably connected at their distal ends directly to said outer margin element, said manipulator tethers or wires being individually or independently manipulable for locating said scaffold in a desired position and conforming said outer margin element to an internal tissue surface.

2. The device or assembly of claim 1, further comprising a delivery catheter for positioning said scaffold into the heart chamber, said scaffold being disposed in a collapsed delivery configuration inside said catheter.

3. The device or assembly of claim 2 wherein said manipulator tethers or wires extend within said delivery catheter, said tethers or wires being attached at distal ends to said outer margin element at spaced locations thereon for maneuvering said scaffold into position by moving said wires or cords independently of one another, said wires or cords being detachable post fixation of said outer margin element of said scaffold to the internal tissue surface.

4. The device or assembly of claim 1, further comprising at least one fastener or fixation mechanism connected to said outer margin element for attaching said outer margin element to an internal tissue surface of a heart chamber.

5. The device or assembly of claim 4 wherein said fastener or fixation mechanism attaches said outer margin element circumferentially all around a perimeter of said outer margin element to the internal tissue surface, creating a continuous or near continuous contact between the internal tissue surface and said scaffold.

6. The device or assembly of claim 1, further comprising a membrane extending between said outer margin element and said inner margin element.

7. The device or assembly of claim 6 wherein said membrane tents away from one side of said scaffold, to provide a space between said scaffold and a native valve.

8. The device or assembly of claim 1, further comprising elements for attachment of a valve or valve prosthesis to the implantable scaffold.

9. The device or assembly of claim 1 wherein a valve or valve leaflets are pre-attached to a circumference of said orifice prior to placement in the desired position.

10. The device or assembly of claim 1, further comprising means for attaching a sub-valvular apparatus of a heart valve to said scaffold.

* * * * *